(12) United States Patent
Myers

(10) Patent No.: US 9,393,154 B2
(45) Date of Patent: Jul. 19, 2016

(54) LASER METHODS FOR CREATING AN ANTIOXIDANT SINK IN THE CRYSTALLINE LENS FOR THE MAINTENANCE OF EYE HEALTH AND PHYSIOLOGY AND SLOWING PRESBYOPIA DEVELOPMENT

(71) Applicant: Raymond I Myers, Collinsville, IL (US)

(72) Inventor: Raymond I Myers, Collinsville, IL (US)

(*) Notice: Subject to any disclaimer, the term of this patent is extended or adjusted under 35 U.S.C. 154(b) by 259 days.

(21) Appl. No.: 13/790,968

(22) Filed: Mar. 8, 2013

(65) Prior Publication Data

US 2014/0121652 A1  May 1, 2014

Related U.S. Application Data

(63) Continuation-in-part of application No. 13/633,154, filed on Oct. 29, 2012, now abandoned.

(60) Provisional application No. 61/552,933, filed on Oct. 28, 2011.

(51) Int. Cl.
*A61B 18/18* (2006.01)
*A61F 9/008* (2006.01)

(52) U.S. Cl.
CPC .............. *A61F 9/008* (2013.01); *A61F 9/00802* (2013.01); *A61F 2009/0087* (2013.01); *A61F 2009/00861* (2013.01); *A61F 2009/00887* (2013.01); *A61F 2009/00891* (2013.01); *A61F 2009/00895* (2013.01)

(58) Field of Classification Search
CPC ................ A61F 9/008; A61F 9/00802; A61F 2009/00887; A61F 2009/00861

USPC ...................... 606/1–19; 607/88–94; 128/898
See application file for complete search history.

(56) References Cited

U.S. PATENT DOCUMENTS

| | | |
|---|---|---|
| 3,971,382 A | 7/1976 | Krasnov |
| 3,982,541 A | 9/1976 | L'Esperance |
| 4,024,852 A | 5/1977 | L'Esperance et al. |
| 4,263,893 A | 4/1981 | Paviak et al. |
| 4,381,007 A | 4/1983 | Doss |
| 4,394,144 A | 7/1983 | Aoki |
| 4,461,294 A | 7/1984 | Baron |
| 4,477,159 A | 10/1984 | Mizuno et al. |
| 4,502,816 A | 3/1985 | Creter et al. |

(Continued)

FOREIGN PATENT DOCUMENTS

WO     2005070358 A1    1/2005

OTHER PUBLICATIONS

Qian, Wen, et al., "3 Year Simvastatin Treatment and Lens Nuclear Back Scattering," J. Ophthalmol, vol. 84, 2000, pp. 512-516.

(Continued)

*Primary Examiner* — Lynsey Crandall
*Assistant Examiner* — Sebastian X Lukjan
(74) *Attorney, Agent, or Firm* — Lewis Rice LLP

(57) ABSTRACT

Systems and methods of laser treatment of the intact crystalline lens to increase ionic transport of antioxidants in specific areas where flexural changes and transparency reduction come from lens aging. Microchannels created in patterns and grids placed strategically in the inner lens carry antioxidants from the source—the anterior and the epithelium—into areas scarce or void of transport mechanisms (and thus scarce of antioxidants). A variety of patterns are utilized to facilitate ions traveling along new pathways.

12 Claims, 12 Drawing Sheets

(56) References Cited

U.S. PATENT DOCUMENTS

| | | |
|---|---|---|
| 4,517,980 A | 5/1985 | Tagnon |
| 4,537,193 A | 8/1985 | Tanner |
| 4,538,608 A | 9/1985 | L'Esperance, Jr. |
| 4,554,917 A | 11/1985 | Tagnon |
| 4,561,436 A | 12/1985 | Munnerlyn |
| 4,565,197 A | 1/1986 | Daly |
| 4,573,778 A | 3/1986 | Shapiro |
| 4,576,160 A | 3/1986 | Tanaka |
| 4,579,430 A | 4/1986 | Bille |
| 4,580,559 A | 4/1986 | L'Esperance |
| 4,582,405 A | 4/1986 | Muller et al. |
| 4,583,539 A | 4/1986 | Karlin et al. |
| 4,588,505 A | 5/1986 | Walley et al. |
| 4,601,037 A | 7/1986 | McDonald |
| 4,601,288 A | 7/1986 | Myers |
| 4,607,622 A | 8/1986 | Fritch |
| 4,628,416 A | 12/1986 | Dewey |
| 4,633,866 A | 1/1987 | Peyman et al. |
| 4,638,801 A | 1/1987 | Daly et al. |
| 4,644,948 A | 2/1987 | Lang et al. |
| 4,648,400 A | 3/1987 | Schneider et al. |
| 4,657,013 A | 4/1987 | Hoerenz et al. |
| 4,665,913 A | 5/1987 | L'Esperance, Jr. |
| 4,669,466 A | 6/1987 | L'Esperance, Jr. |
| 4,669,839 A | 6/1987 | Muchel |
| 4,682,595 A | 7/1987 | Hoerenz et al. |
| 4,686,979 A | 8/1987 | Gruen et al. |
| 4,686,992 A | 8/1987 | Dewey et al. |
| 4,702,245 A | 10/1987 | Schroeder et al. |
| 4,702,576 A | 10/1987 | Magnante |
| 4,711,540 A | 12/1987 | Yoshino et al. |
| 4,711,541 A | 12/1987 | Yoshino et al. |
| 4,712,543 A | 12/1987 | Baron |
| 4,715,703 A | 12/1987 | Cornsweet et al. |
| 4,718,418 A | 1/1988 | L'Esperance, Jr. |
| 4,719,912 A | 1/1988 | Weinberg |
| 4,721,379 A | 1/1988 | L'Esperance, Jr. |
| 4,724,522 A | 2/1988 | Belogorod |
| 4,729,372 A | 3/1988 | L'Esperance, Jr. |
| 4,729,373 A | 3/1988 | Peyman |
| 4,732,148 A | 3/1988 | L'Esperance, Jr. |
| 4,732,460 A | 3/1988 | Kele et al. |
| 4,736,744 A | 4/1988 | Koike et al. |
| 4,741,612 A | 5/1988 | Birngruber et al. |
| 4,758,081 A | 7/1988 | Barnes |
| 4,765,336 A | 8/1988 | Blaha et al. |
| 4,770,162 A | 9/1988 | L'Esperance |
| 4,770,172 A | 9/1988 | L'Esperance, Jr. |
| 4,770,486 A | 9/1988 | Wang et al. |
| 4,772,116 A | 9/1988 | Schroeder et al. |
| 4,773,414 A | 9/1988 | L'Esperance, Jr. |
| 4,775,361 A | 10/1988 | Jacques et al. |
| 4,776,687 A | 10/1988 | Nakanishi et al. |
| 4,798,204 A | 1/1989 | L'Esperance, Jr. |
| 4,820,264 A | 4/1989 | Matsui et al. |
| 4,830,483 A | 5/1989 | Kohayakawa et al. |
| 4,832,043 A | 5/1989 | Ichihashi et al. |
| 4,837,857 A | 6/1989 | Scheller et al. |
| 4,838,266 A | 6/1989 | Koziol et al. |
| 4,840,175 A | 6/1989 | Peyman |
| 4,846,172 A | 7/1989 | Berlin |
| 4,848,340 A | 7/1989 | Bille et al. |
| 4,854,693 A | 8/1989 | Ichihashi et al. |
| 4,856,513 A | 8/1989 | Muller |
| 4,862,888 A | 9/1989 | Yessik |
| 4,863,261 A | 9/1989 | Flammer |
| 4,865,029 A | 9/1989 | Pankratov |
| 4,865,441 A | 9/1989 | Reis |
| 4,866,243 A | 9/1989 | Sakane et al. |
| 4,870,952 A | 10/1989 | Martinez |
| 4,881,808 A | 11/1989 | Bille et al. |
| 4,883,351 A | 11/1989 | Weiss |
| 4,887,019 A | 12/1989 | Reis et al. |
| 4,887,592 A | 12/1989 | Loertscher |
| 4,891,043 A | 1/1990 | Zeimer et al. |
| 4,900,143 A | 2/1990 | Bessler et al. |
| 4,900,145 A | 2/1990 | Akiuama |
| 4,901,718 A | 2/1990 | Bille et al. |
| 4,903,695 A | 2/1990 | Warner et al. |
| 4,905,711 A | 3/1990 | Bennett et al. |
| 4,907,586 A * | 3/1990 | Bille et al. .................. 606/5 |
| 4,911,160 A | 3/1990 | Thyzel |
| 4,911,711 A | 3/1990 | Telfair et al. |
| 4,917,486 A | 4/1990 | Raven et al. |
| 4,931,053 A | 6/1990 | L'Esperance |
| 4,941,093 A | 7/1990 | Marshall et al. |
| 4,951,663 A | 8/1990 | L'Esperance, Jr. |
| 4,953,969 A | 9/1990 | Fedorov |
| 4,966,577 A | 10/1990 | Crosson et al. |
| 4,972,836 A | 11/1990 | Schenck et al. |
| 4,973,330 A | 11/1990 | Azema et al. |
| 4,976,709 A | 12/1990 | Sand |
| 4,988,348 A | 1/1991 | Bille |
| 4,994,058 A | 2/1991 | Raven et al. |
| 5,000,561 A | 3/1991 | Lawniczak et al. |
| 5,000,751 A | 3/1991 | Schroder et al. |
| 5,002,571 A | 3/1991 | O'Donnell et al. |
| 5,013,311 A | 5/1991 | Nouri |
| 5,019,074 A | 5/1991 | Muller |
| 5,041,134 A | 8/1991 | O'Donnell |
| 5,048,946 A | 9/1991 | Sklar et al. |
| 5,049,147 A | 9/1991 | Danon |
| 5,057,102 A | 10/1991 | Tomioka et al. |
| 5,067,951 A | 11/1991 | Greve |
| 5,090,798 A | 2/1992 | Kohayakawa |
| 5,092,863 A | 3/1992 | Schanzlin |
| 5,098,426 A | 3/1992 | Sklar et al. |
| 5,102,409 A | 4/1992 | Balaorod |
| 5,108,388 A | 4/1992 | Trokel |
| 5,108,412 A | 4/1992 | Krumeich et al. |
| 5,112,328 A | 5/1992 | Taboada et al. |
| 5,116,114 A | 5/1992 | Nakamura et al. |
| 5,122,135 A | 6/1992 | Durr et al. |
| 5,123,902 A | 6/1992 | Muller et al. |
| 5,128,509 A | 7/1992 | Black et al. |
| 5,133,708 A | 7/1992 | Smith |
| 5,137,530 A | 8/1992 | Sand |
| 5,141,506 A | 8/1992 | York |
| 5,147,349 A | 9/1992 | Johnson et al. |
| 5,147,352 A | 9/1992 | Azema et al. |
| 5,152,055 A | 10/1992 | L'Esperance et al. |
| 5,152,759 A | 10/1992 | Parel et al. |
| 5,163,934 A | 11/1992 | Munnerlyn |
| 5,171,242 A | 12/1992 | Dewey et al. |
| 5,174,021 A | 12/1992 | L'Esperance et al. |
| 5,178,635 A | 1/1993 | Gwon et al. |
| 5,188,631 A | 2/1993 | L'Esperance, Jr. |
| 5,194,948 A | 3/1993 | L'Esperance et al. |
| 5,196,006 A | 3/1993 | Klopotek et al. |
| 5,196,027 A | 3/1993 | Thompson et al. |
| 5,201,730 A | 4/1993 | Easley et al. |
| 5,203,353 A | 4/1993 | Easley et al. |
| 5,207,668 A | 5/1993 | L'Esperance, Jr. |
| 5,213,092 A | 5/1993 | Uram |
| 5,215,104 A | 6/1993 | Steinert |
| 5,217,459 A | 6/1993 | Kamerling |
| 5,219,343 A | 6/1993 | L'Esperance, Jr. |
| 5,219,344 A | 6/1993 | Yoder, Jr. |
| 5,222,981 A | 6/1993 | Werblin |
| 5,224,942 A | 7/1993 | Beuchat et al. |
| 5,226,903 A | 7/1993 | Mizuno |
| 5,246,435 A | 9/1993 | Bille et al. |
| 5,246,436 A | 9/1993 | Rowe |
| 5,257,988 A | 11/1993 | L'Esperance |
| 5,258,025 A | 11/1993 | Fedorov et al. |
| 5,263,950 A | 11/1993 | L'Esperance |
| 5,263,951 A | 11/1993 | Spears et al. |
| 5,275,593 A | 1/1994 | Easley et al. |
| 5,277,911 A | 1/1994 | Viegas et al. |
| 5,279,298 A | 1/1994 | Flower |
| 5,279,611 A | 1/1994 | McDonnell et al. |
| 5,281,211 A | 1/1994 | Parel et al. |
| 5,282,798 A | 2/1994 | Bruse et al. |
| 5,284,477 A | 2/1994 | Hanna et al. |

(56) References Cited

U.S. PATENT DOCUMENTS

| | | |
|---|---|---|
| 5,288,293 A | 2/1994 | O'Donnell |
| 5,290,272 A | 3/1994 | Burstein et al. |
| 5,295,989 A | 3/1994 | Nakamura |
| 5,300,020 A | 4/1994 | L'Esperance |
| 5,300,061 A | 4/1994 | Easley et al. |
| 5,300,062 A | 4/1994 | Ueno |
| 5,300,063 A | 4/1994 | Tano et al. |
| 5,300,114 A | 4/1994 | Gwon et al. |
| 5,304,168 A | 4/1994 | Sun |
| 5,304,169 A | 4/1994 | Sand |
| 5,311,224 A | 5/1994 | Enomoto |
| 5,312,320 A | 5/1994 | L'Esperance, Jr. |
| 5,312,393 A | 5/1994 | Mastel |
| 5,314,422 A | 5/1994 | Nizzola |
| 5,318,047 A | 6/1994 | Davenport et al. |
| 5,318,560 A | 6/1994 | Blount |
| 5,323,788 A | 6/1994 | Silverstrini et al. |
| 5,324,281 A | 6/1994 | Muller |
| 5,334,190 A | 8/1994 | Seiler |
| 5,336,215 A | 8/1994 | Hsueh et al. |
| 5,336,216 A | 8/1994 | Dewey |
| 5,342,351 A | 8/1994 | Blaha et al. |
| 5,342,370 A | 8/1994 | Simon et al. |
| 5,345,948 A | 9/1994 | O'Donnell |
| 5,347,329 A | 9/1994 | Ota |
| 5,348,551 A | 9/1994 | Spears et al. |
| 5,350,374 A | 9/1994 | Smith |
| 5,354,331 A | 10/1994 | Schachar |
| 5,356,407 A | 10/1994 | Easley et al. |
| 5,356,409 A | 10/1994 | Nizzola |
| 5,360,424 A | 11/1994 | Klopotek |
| 5,364,388 A | 11/1994 | Koziol |
| 5,364,390 A | 11/1994 | Taboada et al. |
| 5,368,590 A | 11/1994 | Itoh |
| 5,370,641 A | 12/1994 | O'Donnell |
| 5,372,595 A | 12/1994 | Gaasterland et al. |
| 5,374,265 A | 12/1994 | Sand |
| 5,376,086 A | 12/1994 | Khoobehi et al. |
| 5,391,165 A | 2/1995 | Fountain et al. |
| 5,395,356 A | 3/1995 | King et al. |
| 5,403,307 A | 4/1995 | Lelman |
| 5,408,484 A | 4/1995 | Weimel |
| 5,411,501 A | 5/1995 | Klopotek |
| 5,412,561 A | 5/1995 | Rosenshein et al. |
| 5,413,555 A | 5/1995 | McMahan |
| 5,423,798 A | 6/1995 | Crow |
| 5,423,800 A | 6/1995 | Ren et al. |
| 5,423,801 A | 6/1995 | Muller et al. |
| 5,425,727 A | 6/1995 | Koziol |
| 5,425,729 A | 6/1995 | Ishida et al. |
| 5,425,730 A | 6/1995 | Luloh |
| 5,437,657 A | 8/1995 | Epstein |
| 5,437,658 A | 8/1995 | Muller et al. |
| 5,439,462 A | 8/1995 | Bille et al. |
| 5,441,496 A | 8/1995 | Easley et al. |
| 5,442,412 A | 8/1995 | Frey et al. |
| 5,442,487 A | 8/1995 | Mizuno |
| 5,445,633 A | 8/1995 | Nakamura et al. |
| 5,460,627 A | 10/1995 | O'Donnell, Jr. |
| 5,461,212 A | 10/1995 | Seiler et al. |
| 5,462,739 A | 10/1995 | Dan et al. |
| 5,465,737 A | 11/1995 | Schachar |
| 5,470,329 A | 11/1995 | Sumiua |
| 5,474,548 A | 12/1995 | Knopp et al. |
| 5,476,511 A | 12/1995 | Gwon et al. |
| 5,480,396 A | 1/1996 | Simon et al. |
| 5,484,432 A | 1/1996 | Sand |
| 5,489,299 A | 2/1996 | Schachar |
| 5,503,165 A | 4/1996 | Schachar |
| 5,507,740 A | 4/1996 | O'Donnell, Jr. |
| 5,514,124 A | 5/1996 | Alpins |
| 5,514,125 A | 5/1996 | Lasser et al. |
| 5,520,679 A | 5/1996 | Lin |
| 5,527,774 A | 6/1996 | Girard |
| 5,529,076 A | 6/1996 | Schachar |
| 5,533,997 A | 7/1996 | Ruiz |
| 5,556,395 A | 9/1996 | Shimmick et al. |
| 5,573,544 A | 11/1996 | Simon et al. |
| 5,594,753 A | 1/1997 | Frey et al. |
| 5,618,284 A | 4/1997 | Sand et al. |
| 5,627,162 A | 5/1997 | Gwon et al. |
| 5,632,742 A | 5/1997 | Frey et al. |
| 5,651,782 A | 7/1997 | Simon et al. |
| 5,656,186 A | 8/1997 | Mourou et al. |
| 5,684,560 A | 11/1997 | Roffman et al. |
| 5,709,868 A | 1/1998 | Perricone |
| 5,722,952 A | 3/1998 | Schachar |
| 5,731,909 A | 3/1998 | Schachar |
| 5,738,677 A | 4/1998 | Colvard et al. |
| 5,752,950 A | 5/1998 | Frey et al. |
| 5,773,472 A | 6/1998 | Stjernschantz et al. |
| 5,828,686 A | 10/1998 | Frey et al. |
| 5,843,184 A | 12/1998 | Cionni |
| 5,849,006 A | 12/1998 | Frey et al. |
| 5,907,908 A | 6/1999 | Cunanan et al. |
| 5,980,513 A | 11/1999 | Frey et al. |
| 6,007,578 A | 12/1999 | Schachar |
| 6,013,101 A | 1/2000 | Israel |
| 6,027,494 A | 2/2000 | Frey |
| 6,055,259 A | 4/2000 | Frey et al. |
| 6,059,772 A | 5/2000 | Hsia et al. |
| 6,099,522 A | 8/2000 | Knopp et al. |
| 6,132,424 A | 10/2000 | Tang |
| 6,190,375 B1 | 2/2001 | Frey |
| 6,197,018 B1 | 3/2001 | O'Donnell, Jr. |
| 6,197,056 B1 | 3/2001 | Schachar |
| 6,252,595 B1 | 6/2001 | Birmingham et al. |
| 6,254,595 B1 | 7/2001 | Juhasz et al. |
| 6,261,220 B1 | 7/2001 | Frey et al. |
| 6,271,914 B1 | 8/2001 | Frey et al. |
| 6,271,915 B1 | 8/2001 | Frey et al. |
| 6,280,468 B1 | 8/2001 | Schachar |
| 6,299,640 B1 | 10/2001 | Schachar |
| 6,302,879 B1 | 10/2001 | Frey et al. |
| 6,312,422 B1 | 11/2001 | Dubnack |
| 6,312,424 B1 | 11/2001 | Largent |
| 6,313,165 B1 | 11/2001 | Grunberger et al. |
| 6,315,773 B1 | 11/2001 | Frey et al. |
| 6,319,274 B1 | 11/2001 | Shadduck |
| 6,322,545 B1 | 11/2001 | Schachar |
| 6,322,556 B1 | 11/2001 | Gwon |
| 6,324,191 B1 | 11/2001 | Horvath |
| 6,325,791 B1 | 12/2001 | Shimoji |
| 6,325,792 B1 | 12/2001 | Swinger et al. |
| 6,344,040 B1 | 2/2002 | Juhasz et al. |
| 6,373,571 B1 | 4/2002 | Juhasz et al. |
| D459,806 S | 7/2002 | Webb |
| D459,807 S | 7/2002 | Webb |
| D462,442 S | 9/2002 | Webb |
| D462,443 S | 9/2002 | Webb |
| 6,451,008 B1 | 9/2002 | Frey et al. |
| 6,460,997 B1 | 10/2002 | Frey et al. |
| 6,493,151 B2 | 12/2002 | Schachar |
| 6,494,910 B1 | 12/2002 | Ganem et al. |
| 6,497,483 B2 | 12/2002 | Frey et al. |
| 6,585,726 B2 | 7/2003 | Frey et al. |
| 6,623,476 B2 | 9/2003 | Juhasz et al. |
| 6,626,893 B2 | 9/2003 | Frey et al. |
| 6,626,894 B2 | 9/2003 | Frey et al. |
| 6,626,895 B2 | 9/2003 | Frey et al. |
| 6,626,896 B2 | 9/2003 | Frey et al. |
| 6,626,897 B2 | 9/2003 | Frey et al. |
| 6,626,898 B2 | 9/2003 | Frey et al. |
| 6,648,877 B1 | 11/2003 | Juhasz et al. |
| 6,669,342 B2 | 12/2003 | Lieberman et al. |
| 6,676,653 B2 * | 1/2004 | Juhasz et al. ............ 606/4 |
| 6,693,927 B1 | 2/2004 | Horvath et al. |
| 6,726,679 B1 | 4/2004 | Dick et al. |
| 6,923,955 B2 | 8/2005 | Till et al. |
| 7,252,662 B2 | 8/2007 | McArdle et al. |
| RE40,420 E | 7/2008 | Dick et al. |
| 2001/0029363 A1 | 10/2001 | Lin |
| 2002/0004658 A1 | 1/2002 | Munnerlyn et al. |
| 2002/0025311 A1 | 2/2002 | Till |

(56) References Cited

U.S. PATENT DOCUMENTS

| | | |
|---|---|---|
| 2002/0049450 A1* | 4/2002 | Myers .......................... 606/107 |
| 2002/0103478 A1 | 8/2002 | Gwon et al. |
| 2002/0110549 A1 | 8/2002 | Till |
| 2002/0138139 A1 | 9/2002 | Till |
| 2002/0140903 A1 | 10/2002 | Schachar |
| 2003/0055412 A1 | 3/2003 | Lieberman et al. |
| 2003/0135272 A1 | 7/2003 | Brady et al. |
| 2003/0139737 A1 | 7/2003 | Lin |
| 2003/0212387 A1* | 11/2003 | Kurtz et al. ...................... 606/4 |
| 2003/0220630 A1 | 11/2003 | Lin et al. |
| 2004/0054359 A1 | 3/2004 | Ruiz et al. |
| 2004/0070761 A1 | 4/2004 | Horvath et al. |
| 2004/0199149 A1* | 10/2004 | Myers et al. ...................... 606/4 |
| 2005/0107775 A1 | 5/2005 | Huang et al. |
| 2005/0165387 A1 | 7/2005 | Lubatschowski et al. |
| 2006/0195076 A1 | 8/2006 | Blumenkranz et al. |
| 2007/0078447 A1 | 4/2007 | Weinacht et al. |
| 2007/0185475 A1 | 8/2007 | Frey et al. |
| 2007/0265603 A1 | 11/2007 | Pinelli |
| 2010/0114079 A1* | 5/2010 | Myers et al. ...................... 606/5 |
| 2011/0202114 A1* | 8/2011 | Kessel et al. .................... 607/88 |

OTHER PUBLICATIONS

Qian, Wen, et al., "Universal Opacity Standard for Scheimpflug Photography," Ophthalmic Res, 2000, vol. 32, pp. 292-298.
Rockwell, B. A., et al., "Safe Use of Ultrashort Lasers," SPIE, vol. 3616, 1999, pp. 32-39.
Roi, Pascal, et al., "An Optomechanical Eye Model for Observation of Lens Photoablation," SPIE, 1997, vol. 2971, pp. 171-174.
Sacks, Zachary S., et al., "Laser Spot Size as a Function of Tissue Depth and Laser Wavelength in Human Sclera," SPIE, 1998, vol. 3255, pp. 67-76.
Scammon, Richard J., et al., "Simulations of Shock Waves and Cavitation Bubbles Produced in Water by Picosecond and Nanosecond Laser Pulses," SPIE, 1998, vol. 3254, pp. 264-275.
Schachar, Ronald A. MD, et al., "Mechanism of Human Accommodations as Analyzed by Nonlinear Finite Element Analysis," Ann. Opthalmol, 2001, vol. 33, No. 2, pp. 103-112.
Schaeffel, Frank, "Kappa and Hirschberg Ration Measured With an Automated Video Gaze Tracker," Optometry and Vision Science, 2002, vol. 79, No. 5, pp. 329-334.
Schaffer, Chris B., et al., "Dynamics of Femtosecond Laser-Induced Breakdown in Water From Femtoseconds to Microseconds," Optics Express, 2002, vol. 10, No. 3, pp. 196-203.
Shen, Nan, "Photodisruption in Biological Tissues Using Femtosecond Laser Pulses," A Thesis Presented to the Department of Physics, Harvard University, 2003, pp. 1-125.
Sher, Neal A. MD, "Hyperopic Refractive Surgery," Current Opinion in Ophthalmology, 2001, vol. 12, pp. 304-308.
Soderberg, Per G., et al., "Angular Dependence of the Intensity of Back Scattered Light From Human Lenses with Nuclear Cataract, Implications for Measurement," SPIE, 2000, vol. 3908, pp. 34-37.
Soderberg, Per G., et al., "External Standard for Measurements with the Scheimpflug Slitlamp Microscope," SPIE, 1997, vol. 2971, pp. 8-13.
Stilzel,Joel D., et al, "A Nonlinear Finite Element Model of the Eye with Experimental Validation for the Prediction of Globe Rupture," Stapp Car Crash Journal, 2002, vol. 45, 24 pgs.
Strauss, Moshe, et al., "Two-Dimensional Rayleigh Model of Vapor Bubble Evolution," SPIE, 1999, vol. 3601, pp. 212-224.
Strenk, Susan A., et al., "Age-Related Changes in Human Ciliary Muscle and Lens: A Magnetic Resonance Imaging Study," Investigative Ophthalmology & Visual Science, 1999, vol. 40, No. 6, pp. 1162-1169.
Sweeney, Matthew H. J., et al., "Movement of Cysteine in Intact Monkey Lenses: The Major Site of Entry is the Germinative Region," Experimental Eye Research, 2003, vol. 77, pp. 245-251.
Tahi, Hassan, et al., "Restoring Accommodation: Surgical Technique and Preliminary Evaluation in Rabbits," SPIE 1999, vol. 3591, pp. 267-269.
Tang, Daxin, "Influence of Age, Diabetes and Cataract on Calcium, Lipid-Calcium and Protein-Calcium Relationships in Human Lenses," Investigative Ophthalmology & Visual Science, 2003, vol. 44, No. 5, pp. 2059-2066.
Vilupuru, Abhiram S., "Optical and Biometric Relationships of the Isolated Pig Crystalline Lens," Ophthal. Physiol. Opt., 2001, vol. 21, No. 4, pp. 296-311.
Vogel, Alfred, et al., "Interaction of Laser-Produced Cavitation Bubbles with Elastic Tissue Model," SPIE, 2001, vol. 4257, pp. 167-177.
Vogel, Alfred, et al., "Numerical Simulation of Optical Breakdown for Cellular Surgery at Nanonsecond to Femtosecond Time Scales," SPIE, 2001, vol. 4433, pp. 70-80.
Vogel, Alfred, et al., "Laser-Induced Breakdown in the Eye at Pulse Durations from 80 ns To 100fs," SPIE, 1998, vol. 3255, pp. 34-49.
Vogel, Alfred, et al., "Kinetics of Phase Transitions in Pulsed IR Laser Ablation of Biological Tissues," SPIE, 2003, vol. 4961, pp. 66-74.
Fisher, R F, "The Ciliary Body in Accommodation," Trans. Opthalmol Soc. UK, 1989, 105 (Pt2): 208-19, 1 page.
Garner, LF, et al., "Changes in Ocular Dimensions and Refraction with Accommodation," Opthalmic Physiol. Opt., 1997, 17(1): 12-7, 1 page.
McCourt, ME, et al., "Refractive State, Depth of Focus, and Accommodation of the Eye of the California ground squirrel (Spermophiliu beecheyi)" Vision Res., 1984, 24(10):1261-6, 1 page.
Avro, "Statement of the Use of Animals in Opthalmic and Visual Research," The Association for Research in Vision and Opthalmology, copyright © 2002, obtained from the Internet on Jan. 15, 2005 at http://www.avro.org/AboutAvro/anamlst.asp, 3 pages.
Breitenfeld, P., et al., "Finite Element Method-Simulation of the Human Lens during Accomodation," Therapeutic Laser Applications and Laser-Tissue Interactions II, Proceedings of the SPIE, 2005, pp. 1-9, vol. 5863.
Ripken, T., et al., "First in-vivo studies of presbyopia treatment with ultrashort laserpulses," Therapeutic Laser Applications and Laser-Tissue Interactions, Proceedings of the SPIE, 2003, pp. 137-145, vol. 5142.
Ripken, T., et al., "Investigations for the correction of presbyopia by fs-laser induced cuts," Ophthalmic Technologies XIV, Proceedings of the SPIE, 2004, pp. 27-35, vol. 5314.
Shui, Ying-Bo, et al., "Oxygen Distribution in the Rabbit Eye and Oxygen Consumption by the Lens," IVOS, Apr. 2006, pp. 1571-1580, vol. 47, No. 4.
Garner, LF, et al., "Changes in Equivalent and Gradient Refractive Index of the Crystalline Lens and Accomodation," Optom Vis Sci, 1997, 74(2): 114-9, Abstract only.
Glasser, Adrian, et al., "Presbyopia and the Optical Changes in the Human Crystalline Lens with Age," Vision Res., 1998, pp. 209-299, vol. 38, No. 2.
Beebe, David C., et al., "Reply to: A Critical Appraisal of the Lens Circulation Model—An Experimental Paradigm for Understanding the Maintenance of Lens Transperancy?," IVOS, May 2010, p. 2312, vol. 51, No. 5.
Giblin, Frank J., "Glutathione: A Vital Lens Antioxidant," Journal of Ocular Pharmacology and Therapeutics, 2000, pp. 121-135, two reference pages, vol. 16, No. 2, Mary Ann Liebert, Inc.
Siegfried, Carla J., et al., "Oxygen Distribution in the Human Eye: Relevance to the Etiology of Open-Angle Glaucoma After Vitrectomy," IVOS, Nov. 2010, pp. 5731-5738, vol. 51, No. 11.
Sweeney, Matthew H. J., et al., "An Impediment to Glutathione Diffusion in Older Normal Human Lenses: a Possible Precondition for Nuclear Cataract," Exp. Eye Res., 1998, 67, 587-595.
Heys, Karl Robert, et al., "Massive increase in the stiffness of the human lens nucleus with age: the basis for presbyiopia?," Molecular Vision, 2004, 10:956-63.
Bai, F., et al., Abstract, http://www.absractsonline.com/Plan/ViewAbstract.aspx?sKey=88fb6.., printed on Oct. 25, 2012, two pages.
Melberg, Nancy S. et al., "Nuclear Sclerotic Cataract after Vitrectomy in Patients Younger than 50 Years of Age," Opthamology, 1995, 102: 1466-1471.

(56) References Cited

OTHER PUBLICATIONS

Van De Sompel, Dominique, et al., "Model of accomodation: Contributors of lens geometry and mechanical properties to the development of presbyopia," J. Cataract Refract Surg, Nov. 2010, pp. 1960-1971, vol. 36.
Heys, Karl R., et al., "The stiffness of human cataract lenses is a function of both age and the type of cataract," Experimental Eye Research, 2008, 86: 701-703.
Krueger, Ronald R., et al., "Experimental Increase in Accomodative Potential after Neodymium: Yttrium-Aluminium-Garnet Laser Photodisruption of Paired Cadaver Lenses," American Academy of Ophthalmology, 2001, pp. 2122-2129.
Kusak, Jer R., et al., "Development of lens sutures," Int. J. Dev. Biol., 2004, 48: 889-902.
Maguire, Albert M., et al., "Lens-Sparing Vitreoretinal Surgery in Infants," Arch Ophthalmol, Feb. 1992, pp. 284-286, vol. 110.
Cazabon, Sunildath, et al., "Intralenticular metallic foreign body," J Cataract Refract Surg, Dec. 2002, 28: 2233-2234.
Moshfeghi, Andrew A., et al., "Lens-Sparing Vitrectomy for Progressive Tractional Retinal Detachments Associated With Stage 4A Retinopathy of Prematurity," Arch Ophthalmol, Dec. 2004, pp. 1816-1818, vol. 122.
Myers, Raymond I., et al., "Novel Approaches to Correction of Presbyopia with Laser Modification of the Crystalline Lens," Journal of Refractive Surgery, Mar./Apr. 1998, pp. 136-139, vol. 14.
Palmquist, Britt-Marie, et al., "Nuclear cataract and myopia during hyperbaric oxygen therapy," British Journal of Ophthalmology, 1984, 68: 113-177.
Akchurin, Gairf, et al., "Evaluation of the degree of turbidity of cataract lens and its correlation with retinal visual acuity," SPIE, vol. 3591, 1999, pp. 74-81.
Amann, Josef, et al., "Increased Endothelial Cell Density in the Paracentral and Peripheral Regions of the Human Cornea," American Journal of Ophthalmology, vol. 135, No. 5, 2003, pp. 584-590.
Amendt, M. Strauss, et al., "Modeling of Bubble Dynamics in Relation to Medical Applications," SPIE, vol. 2975, 1997, pp. 362-373.
Ansari, Rafat R., et al., "Measuring Lens Opacity: Combining Quasi-Elastic Light Scattering With Scheimpflug Imaging System," SPIE, vol. 3246, 1998, pp. 35-42.
Apple, David J., et al., "Preparation and Study of Human Eyes Obtained Postmortem with the Miyake Posterior Photographic Technique," Ophthalmology, vol. 97, No. 6, 1990, pp. 810-816.
Barak, Adiel, et al., "Anterior Capsulotomoy Using the CO2 Laser," SPIE, vol. 3246, 1998, pp. 196-198.
Balaram, Mini, et al., Noncontact Specular Microscopy of Human Lens Ephitelium, IOVS, vol. 41, No. 2., 2000, pp. 474-481.
Ben-Sira, I., et al., "Clinical Method for Measurement of Light Backscattering from the in vivo human lens," Invest. Ophthalmology Vis. Sci., vol. 19, No. 4 (Reports), 1980, pp. 435-437.
Benjamin, William J., "Borish's Clinical Refraction," W. B. Saunders, publishers, copyright 1998, p. 110.
Bettleheim, Frederick A., et al., "Syneretic Response of Aging Normal Human Lens to Pressure," Investigative Ophthalmology & Visual Science, Vo. 44, No. 1, 2003, pp. 258-263.
Bito, L.Z., et al., "Age-Dependent Loss of Accomodative Amplitude in Rhesus Monkeys: An Animal Model for Presbyopia," Invest. Ophthalmol. Vis. Sci., vol. 23, No. 1, 1982, pp. 23-31.
Breitling, Detlef, et al., "Fundamental Aspects in Machining of Metals with Short and Ultrashort Laser Pulses," SPIE, vol. 5339, pp. 1-15.
Burd, H.J., et al., "Numerical Modeling of the Accommodating Lens," Vision Research, vol. 42, 2002, pp. 2235-2251.
Carey, James, et al., "Propogation and Characterization of Ultrashort Laser Pulses," Spectroscopy of Systems with Spatially Confined Structures, Ed. Rino Di Bartolo, Kluwer Academic Press, Netherlands, 2003, pp. 1-30.
Chen, Wei-Li, et al., "Ultrasound Biomicroscopic Findings in Rabbit Eyes Undergoing Scleral Suction during Lamellar Refractive Surgery," IOVS, vol. 43, No. 12, 2002, pp. 3665-3672.

Clafin, E.S., et al., "Configuring an Electrostatic Membrane Mirror by least-squares fitting with analytically derived influence functions," J. Opt. Soc. Am. A., vol. 3, No. 11, 1986, pp. 1833-1839.
Coleman, D. Jackson, et al., "Presbyopia, Accommodation, and the Mature Catenary," Ophthalmology, vol. 108, No. 9, 2001, pp. 1544-1551.
Crawford, Kathryn S., et al., "The Role of the Iris in Accomodation of Rhesus Monkeys," Investigative Opthalmalogy & Visual Science, vol. 31, vol. 10, 1990, pp. 2185-2190.
Czygan, G., et al., "Mechanical Testing of Isolated Senile Human Eye Lens Nuclei," Med. Eng. Phys., vol. 18, No. 5, 1996, pp. 345-349.
Datta, Beajyoti, "Tissue Surgery and Subcellular Photodisruption with Femtosecond Laser Pulses," Thesis for Dept. of Physics, Harvard University, 2002, pp. 1-74.
Dausinger, Freidrich, et al., "Micro-maching with Ultrashort Laser Pulses: From Basic Understanding to Technical Application," SPIE, No. 5147, 2002, pp. 1-10.
Douven, Lucen F.A., et al., "Characterisation of Mechanical Behaviour of Human Skin in vivo," SPIE, vol. 3914, 2000, pp. 618-629.
El-Osta, Austen A. R., et al., "In Vitro Model for the Study of Human Posterior Capsule Opacification," J. Cataract Refract Surg, vol. 29, 2003, pp. 1593-1600.
Gayen, Tapan K, et al., "Near-Infrared Laser Welding of Aortic and Skin Tissues and Microscopic Inventigation of Welding Efficacy," SPIE, vol. 4949, pp. 182-185.
Gershenzon, A., et al., "Clinical and Epidemilogy—New Software for Lens Retro-Illumination Digital Image Analysis," Australian and New Zealand Journal of Ophthalmology, 1999, vol. 27, pp. 170-172.
Glasser, Adrian, et al., "On Modeling the Causes of Presbyopia," Vision Research, 2001, vol. 41, pp. 3083-3087.
Glasser, Adrian, et al., "Ultrasound Biomicroscopy of the Aging Rhesus Monkey Ciliary Region," Optometry and Vision Science, 2001, vol. 78, No. 6, pp. 417-424.
Grace, Jeffrey M., et al., "Repetitively Pulsed Ruby Lasers as Light Sources for High-Speed Photography," Optical Engineering, vol. 37, No. 8, 1998, pp. 1-26.
Hamaoui, Marie, et al., "Ex-vivo Testing of Crystalline Lens Substitutes: A Pilot Study," SPIE, vol. 3908, 2000, pp. 123-130.
Hartwick, Andrew T. E., et al., "Ephitelial Activity of Hexokinase and Glucose-6 Phosphate Dehydrogenase in Cultured Bovine Lenses Recovering from Pharmaceutical-Induced Optical Damage," Molecular Vision, vol. 9, 2003, pp. 594-600.
Heisterkamp, Alexander, et al., "Nonlinear Effects Inside Corneal Tissue after FS-Photodisruption," SPIE, vol. 4433, 2001, pp. 55-60.
Ho, A., et al., "Feasibility of Simultaneous Correction of Ametropia by Varying Gel Refractive Index with Phaco-Ersatz," SPIE, vol. 4245, 2001, pp. 119-128.
Holzer, Mike P., et al., "Corneal Flap Complications in Refractive Surgery—Part 1: Development of an Experimental Animal Model," J. Cataract Refract Surg, vol. 29, 2003, pp. 795-802.
Holzer, Mike P., et al., "Corneal Flap Complications in Refractive Surgery—Part 2: Postoperative Treatments of Diffuse Lamellar Keratitis in an Experimental Animal Model," J. Cataract Refract Surg, vol. 29, 2003, pp. 803-807.
Juhasz, T., et al., "Time-Resolved Studies of Plama-Mediated Surface Ablation of Soft Biological Tissue with Near-Infrared Picosecond Laser Pulses," SPIE, vol. 2975, 1997, pp. 271-281.
Kasthurirangan, Sanjeev, "Amplitude Dependent Accommodative Dynamics in Humans," Vision Research, vol. 43, 2003, pp. 2945-2956.
Koopmans, Steven A., et al., "Polymer Refilling of Presbyopic Human Lenses in Vitro Restores the Ability to Undergo Accommodative Changes," IOVS, vol. 44, No. 1, 2003, pp. 250-257.
Krag, Susanne, "Biomechanical Measurements of the Lens Capsule," Scandinavian University Thesis, 1999.
Krag, Susanne, et al., "Mechanical Properties of the Human Posterior Lens Capsule," IOVS, vol. 44, No. 2, 2003, pp. 691-696.
Krauss, Joel, et al., "Laser Interactions with the Cornea," Survey of Ophthalmology A167, vol. 31, No. 1, 1986, pp. 37-53.
Krueger, Ronald R., et al, "Experimental Increase in Accommodative Potential After Neodymium: Yttrium—Aluminum-Garnet Laser

(56) References Cited

OTHER PUBLICATIONS

Photodisruption of Paired Cadaver Lenses," Ophthalmology vol. 108. No. 11, 2001, pp. 2122-2129.
Kuizenga, Dirk J., "FM-Laser Operation of the Nd:YAG Laser," IEEE Journal of Quantum Electronics, vol. 6, No. 11, 1970, pp. 673—[Check].
Kurtz, Ron, et al., "Femtosecond Laser Corneal Refractive Surgery," SPIE, vol. 3591, 1999, pp. 209-219.
Kurtz, Ron, et al., "Ophthalmic Application of Femtosecond Lasers," SPIE, vol. 3616, 1999, pp. 51-65.
Kurtz, Ron, et al. "Optimal Laser Parameters for Intrastromal Corneal Surgery," SPIE, vol. 3255, 1998, pp. 56-66.
Kuszak, J.R., et al., "A Quantitative Analysis of Sutural Contributions to Variability in Back Vertex Distance and Transmittance in Rabbit Lenses as a Function of Development, Growth and Age," Optometry and Vision Science, vol. 73, No. 3, 2002, pp. 193-204.
Kuszak, J. R., et al., "Electron Microscope Observations of the Crystalline Lens," Microscopy Research and Technique, 1996, vol. 33, pp. 441-479.
Kuszak, J.R., et al., "Quantitative Analysis of Animal Model Lens Anatomy: Accommodative Range is Related to Fiber Structure and Organization," Dept. of Ophthalmology and Pathology, undated, 26 pgs.
Kuszak, J. R., et al., "Suppression of Post-Vitrecetomy Lens Changes in The Rabbit by Novel Benzopyranyl Esters and Amides," Exp. Eye Res., vol. 75, 2002, pp. 459-473.
Kuszak, J. R., et al., "The Relationship Between Rabbit Lens Optical Quality and Sutural Anatomy after Vitrectomy," Exp. Eye Res., vol. 71, 2000, pp. 267-281.
L'Esperance, Jr., Opthalmic Lasers Photocoagulation, Photoradiation and Surgery, 2nd Ed., copyright 1983, The C.V. Mosby Company, pp. 529-538.
Liu, Xinbing, et al., "In vivo Plasma-mediated Ablation as a Function of Laser Pulsewidth," SPIE, vol. 2975, 1997, pp. 282-288.
Loerscher, Hanspeter, et al., "Noncontact Trephination of the Cornea Using a Pulsed Hydrogen Floride Laser," American Journal of Ophthalmology, vol. 104, pp. 471-475.
Losesl, Frieder H., et al., "Laser-Induced Optical Breakdown on Hard and Soft Tissues and its Dependence on the Pulse Duration: Experiment and Model," IEEE Journal of Quantum Electronics, vol. 32, No. 10, 1996, pp. 1717-1722.
Masters, B.R., "Three Dimensional Microscopic Tomographic Imaging of the Cataract in a Human Lens In Vivo," Optics Express, 332, vol. 3, No. 9, 1998, pp. 332-338.
Mathias, R.T., et al., "Physiological Properties of the Normal Lens," Physiological Review, vol. 77, No. 1, 1997, pp. 21-50.
Michael, Ralph, et al., "Refractive Index of Lens Fiber Membranes in Different Parts of the Crystalline Lens," Proceedings of SPIE, Vo. 4611, 2002, pp. 159-164.
Marion II, John E., et al., "Medical Applications of Ultra-Short Pulse Lasers," SPIE, vol. 3616, 1999, pp. 42-50.
Moffatt, B. A., et al., "Age-Related Changes in Refractive Index Distribution and Power of the Human Lens as Measured by Magnetic Resonance Micro-Imaging in Vitro," Vision Research, vol. 42, 2002, pp. 1683-1693.
Neev, Joseph, "Ultrashort Pulse Lasers: A New Tool for Biomedical Applications," SPIE, Vo. 3255, pp. 2-7.
Oberheide, Uwe, et al., "Therapy Monitoring of Laser Cyclophotocoagulation," Proceedings of SPIE, vol. 4611, 2002, pp. 48-53.
Oriowo, Olanrewaju Matthew, "A Study of Ultraviolet Radiation Effects on Procine Crystalline Lens and Development of a New Assay Methodology for UV Cataractogensis Investigation," A Thesis Presented to the University of Waterloo, 2000, pp. i-xix and 1-218.
Parel, Jean Marie, et al., "Intraocular Implants for the Surgical Correction of Presbyopia," In Opthalmic Technologies X, Proceedings of SPIE, vol. 3908, 2000, pp. 115-122.
Payne, Peter A., et al., "Ophthalmic Applications of Laser-Generated Ultrasound," SPIE, vol. 3908, 2000, pp. 13-22.
Peterson, Jennifer A., et al., "Intraocular Pressure Measurement in Cynomolgus Monkeys, Tono-Pen Versus Manometry," Investigative Opthalmology & Visual Science, 1996, vol. 37, No. 6, pp. 1197-1199.
Cook, Christopher A., et al., "Aging of the Human Crystalline Lens and Anterior Segment," Vision Res., vol. 34, No. 22, pp. 2945-2954, 1994.
Koretz, Jane F., et al. "The Zones of Discontinuity in the Human Lense: Development and Distribution with Age," Vision Res., vol. 34, No. 22, pp. 2955-2962, 1994.
Borkman, Raymond F., et al., "Evidence of a Free Radical Mechanism in Aging and u.v.-Irradiated ocular lens," Exp. Eye Res., 1977, pp. 303-309, vol. 25.
Bron, A.J., et al., "The Ageing Lens," Ophthalmologica, 2000, pp. 86-104, vol. 214.
Brown, N., "The Change in Lens Curvature with Age," Exp. Eye Res., 1974, pp. 175-183, vol. 19.
Brown, N., "The Change in Shape and Internal Form of the Lens of the Eye on Accommodation," Exp. Eye Res., 1973; pp. 441-459, vol. 15.
Fagerholm, Per P.P., "The response of the Lens to Trauma," Trans Ophthalmol Soc UK, 1982, pp. 369-374. vol. 102.
Farnsworth, P. N., "Anterior Zonular Shifts with Age," Exp. Eye Res., 1979, pp. 291-297, vol. 28.
Fisher, R. F., "The Elastic Constants of the Humans Lens," J Physiol., 1971, pp. 147-180, vol. 212.
Fisher, R. F., "Presbyopia and the Changes with Age in the Human Crystalline Lens," J Physiol., 1973, pp. 765-779, vol. 288.
Fisher, R. F., "The Mechanics of Accommodation in Relation to Presbyopia," Eye, 1988, pp. 646-649, vol. 2.
Giblin, Frank J., et al., "Nuclear Light Scattering, Disulfide Formation and Membrane Damage in Lenses of Older Guinea Pigs Treated with Hyperbaric Oxygen," Exp. Eye Res., 1995, pp. 219-235, vol. 60.
Gimbel, Howard V., et al., "Intrastromal Photorefractive Keratectomy with the Nd:YLF Laser," Int Ophthal Clin., 1994, pp. 139-145.
Fleck, et al., "Q-switched Nd:YAG laser disruption of rabbit lens nucleus," Laser and Light in Ophthalmology, 1990, pp. 227-232, vol. 3, No. 3.
Gwon, Arlene, et al., "Focal laser photophacoablation of normal and cataractous lenses in rabbits: Preliminary report," J Cataract Refract Surg., 1995, pp. 282-286, vol. 21.
Habib, Maged S., et al., "Myopic Intrastromal Photorefractive Keratectomy With the Neodymium—Yttrium lithium Fluoride Picosecond Laser in the Cat Cornea," Arch Ophthalmol, Apr. 1995, pp. 499-505, vol. 113.
Hahn, D.W., et al., "Dynamics of Ablation Plume Particles Generated During Excimer Laser Corneal Ablation," Lasers in Surgery and Medicine, 1995, pp. 384-389, vol. 16.
Juhasz, Tibor, et al., "Dynamics of Shock Waves and Cavitation Bubbles Generated by Picosecond Laser Pulses in Corneal Tissue and Water," Lasers in Surgery and Medicine, 1994, pp. 91-98, vol. 15.
Keeney, Arthur H., "Intralenticular Foreign Bodies," Arch Ophthalmol., 1971, pp. 499-501, vol. 86.
Koretz, Jane F., et al., "The Zones of Discontinuity in the Human Lens: Development and Distribution with Age," Vision Res., 1994, pp. 2955-2962, vol. 34, No. 22.
Koretz, Jane F., et al., "Analysis of Human Crystalline Lens Curvature as a Function of Accommodative State and Age," Vision Res., 1984, pp. 1141-1151, vol. 24, No. 10.
Koretz, Jane F., et al., "Model of the Accommodative Mechanism in the Human Eye," Vision Res., 1982, pp. 917-927, vol. 22.
Koretz, Jane F., "How the Human Eye Focuses," Scientific American, Jul. 1988, pp. 92-98, vol. 259.
Krueger, Ronald R., et al., "Ultrastructure of Picosecond Laser Intrastromal Photodisruption," Journal of Refractive Surgery, Jul./Aug. 1996, pp. 607-612, vol. 12.
Kurtz, Ron M., et al., "Photodisruption in the Human Cornea as a Function of Laser Pulse Width," Journal of Refractive Surgery, Nov./Dec. 1997, pp. 653-658, vol. 13.
Kuszak, J. R., et al., "Lens Optical Quality is a Direct Function of Lens Sutural Architecture," Invest Ophthal Vis Sci, Jun. 1991, pp. 2119-2129, vol. 32, No. 7.

(56) References Cited

OTHER PUBLICATIONS

Lerman, Sidney, "Photosensitizing Drugs and Their Possible Role in Enhancing Ocular Toxicity," Ophthalmol, 1986, pp. 304-318, vol. 93, No. 3.

Lim, Seung Jeong, et al., "Analysis of zonular-free zone and lens size in relation to axial length of eye with age," J Cat Refract Surg, Mar. 1998, pp. 390-396, vol. 24.

Lutze, Margaret, et al., "Lenses of Diabetic Patients "Yellow" at an Accelerated Rate Similar to Older Normals," Invest Ophthalmol Vis Sci., Jan. 1991, pp. 194-199, vol. 32, No. 1.

Pau, Hans, et al., "The increasing sclerosis of the human lens with age and its relevance to accommodation and presbyopia," Graefe's Arch Clin Exp Ophthalmol, 1991, pp. 294-296, vol. 229.

Puliafito, Carmen A., et al., "High-Speed Photography of Excimer Laser Ablation of the Cornea," Arch Ophthalmol, Sep. 1987, pp. 1255-1259.

Schachar, Ronald A., "Cause and Treatment of Presbyopia With a Method for Increasing the Amplitude of Accommodation," Ann Ophthalmol, 1992, pp. 24:445-452, vol. 24.

Schachar, Ronald A., et al., "Experimental Destruction of Cataractous Lenses by Laser," Surgical Forum, 1973, pp. 506-508, vol. 24.

Schachar, Ronald A., et al., "Experimental Support for Schachar's Hypothesis of Accommodation," Ann Ophthalmol, 1993, pp. 404-409, vol. 25.

Srinivasan, R., "Ablation of Polymers and Biological Tissue by Ultraviolet Lasers," Science, 1986, pp. 559-565, vol. 234.

Spector, Abraham, "Aging of the Lens and Cataract Formation," Aging and Human Visual Function, 1982, pp. 27-43, Alan R. Liss, Inc.

Taylor, Virginia L., et al., "Morphology of the Normal Humans Lens," Invest Ophthal & Vis Sci., Jun. 1996, pp. 1396-1410, vol. 37, No. 7.

Vrensen, G. F. J. M., "Aging of the human eye lens—A morphological point of view," Comp Biochem Physiol, 1995, pp. 519-532, vol. 111A.

Waring, George O., "Presbyopia and Accommodative Intraocular Lenses-the Next Frontier in Refractive Surgery?", Ref & Corneal Surg, Nov./Dec. 1992, pp. 421-422, vol. 8.

Werblin, Theodore P., "Should We Consider Clear Lens Extraction for Routine Refractive Surgery?", Ref & Corneal Surg., Nov./Dec. 1992, pp. 480-481, vol. 8.

Zuclich, Joesph A., "A comparison of laser-induced retinal damage from infrared wavelengths to that from visible wavelengths," Lasers and Light Ophth, 1997, pp. 15-29, vol. 8, No. 1.

Braham, Lewis, "Eye Surgery: It's Getting Sharper," Business Week, Oct. 18, 2004, pp. 142, 145.

Aston, Adam, "Why Settle for 20/20? A new diagnostic tool and laser surgery promise eagle vision," Business Week, Mar. 17, 2003, pp. 95-96.

Cromie, William J., "Laser Makes History's Fastest Holes," The Harvard University Gazettem http://www.news.harvard.edu/gazette/1999/10.07/laser.html, Nov. 22, 1999, 6 pages.

\* cited by examiner

Eye A

Normal Lens and Vitreous

Eye B

Presbyopic Eye with Vitrectomy

Eye C

Non-presbyopic Eye with Vitrectomy

Eye D

Intraocular Lens with vitrectomy

Effects on the Eye with or/ without presence of vitreous and lens

LASER METHODS FOR CREATING AN ANTIOXIDANT SINK IN THE CRYSTALLINE LENS FOR THE MAINTENANCE OF EYE HEALTH AND PHYSIOLOGY AND SLOWING PRESBYOPIA DEVELOPMENT

CROSS REFERENCE TO RELATED APPLICATION(S)

This application is a Continuation-in-Part of U.S. Utility patent application Ser. No. 13/663,154, filed Oct. 29, 2012 and currently pending, which claims the benefit of U.S. Provisional Patent Application Ser. No. 61/552,933, filed Oct. 28, 2011. The entire disclosures of both these documents are incorporated herein by reference.

BACKGROUND

1. Field of the Invention

This disclosure is related to the field of systems and methods for optical lens reformation. Specifically, this disclosure is related to the field of systems and methods for using electromagnetic energy to make physical and biochemical alterations to the ocular lens of a mammalian eye for the correction of visual impairments.

2. Description of Related Art

Cataracts are areas of opacification of the ocular lens of sufficient size to interfere with vision. They have been extensively studied because of their high prevalence in geriatric populations. Cataracts in the aged (senile cataracts) are the most common type, and are often thought to be due to an acceleration of the scattering of light as it passes through the lens of an eye. Cataracts occur to varying extents in all humans over the age of 50, but generally do not cause significant visual dysfunction until the ages of 60-80 years. In some instances, however, cataracts can occur much earlier as a result of risk factors including congenital disease, trauma, and family history.

FIG. 2 and FIG. 3 are presented as an aid to understanding the visual impairments related to the ocular lens, such as the formation of cataracts. The ocular lens is a multi-structural system as illustrated in FIGS. 2 and 3. As will be understood by those of ordinary skill in the art, the macroscopic lens structure includes a cortex just inside the capsule, which is the outer membrane that envelops the other interior structures of the lens. The nuclei are formed from successive additions of the cortex (13) to the nuclear regions, which are subdivided into a deep fetal nucleus (22) which develops in the womb, an infantile nucleus (24), a juvenile nucleus (26), and the adult nucleus (28). On the microscopic level, the structure of the nuclei is layered, resembling the structure of an onion with the oldest layers and cells towards the center (and as depicted in FIG. 2). Rather than being spherical, the lens is a bioconvex shape as shown in FIG. 2. The cortex and the different nuclei have specific structures that are consistent through different ages for specific cell sizes, compactions and clarity. The lens epithelium (23) forms at the lens equatorial region (21) generating ribbon-like cells or fibrils that grow anteriorly and posteriorly around the ocular lens. The unique formation of the crystalline lens is the biconvex shape depicted in FIG. 3 where the ends of the cells align to form a suture in the central and paracentral areas (29) both anteriorly and posteriorly. Transparency is maintained by the regular architecture of the fibrils. As long as the regular architecture is maintained, light passes unobstructed through the lens. The older tissue in both the cortex and nucleus has reduced cellular function, having lost their cell nuclei and other organelles several months after cell formation. The aqueous (17), the liquid in the anterior chamber between the lens and cornea which also contains ionic components and solutes, flows through the lens capsule (14) and sutures. From there, the ions and/or fluids travel into more remote areas of the lens and provide the nutrients needed for minimal cellular life functions, including the removal of toxic and oxidative byproducts.

The microstructure of the fibrils contains interconnections between the ribbon-like fibrils, called balls and sockets, and interdigitations and imprints, which to some extent inhibit the relative motion of fibrils with respect to one another. Still, the fibrils are relatively free to move in relation to each other in the young, flexible crystalline lens. As the eye ages, there are age related changes to these structures that include the development of intracellular bonding, mostly disulfide bonding, the compaction of tissue, the breakdown of some of the original attachments, and the yellowing or darkening of older lens areas.

Changes in the size and shape of the macroscopic lens components throughout life include both the increased curvature and general enlargement of the biconvex lens with age. The thickness of the posterior portion increases more than the anterior portion. Additionally, thickness increases are proportionately greater in the periphery.

The above-mentioned intracellular bonding that occurs with age generally immobilizes the oldest and deepest lens tissue. However, intracellular disulfide bonds are weaker chemical bonds, and are subject to modification and breakage with minute laser pulses. The disulfide bonds are largely formed by the effects of ambient ultraviolet (UV) light from external exposure and from the continual, unrelenting reduction in lens movement with age (presbyopia). The lens absorbs ions and nutrients from the aqueous, a process enhanced by lens accommodation; e.g., the undulating movement of the younger crystalline lens. The aqueous normally contains the amino acid building blocks of antioxidants that aid in preventing disulfide bond formation that further inhibits lens movement and, accordingly, loss of ion and nutrient absorption can lead to presbyopia, cataracts, glaucoma and other related eye conditions.

In summary, presbyopia, light scattering and cataractogenesis generally result from intrafibril attachment. On the cellular level, all cataracts begin with oxidative changes of the crystalline tissue. The changes in the lens tissue that lead to light scattering occur when individual fibers combine to form large, light-disrupting macromolecular complexes.

Generally, the two different processes that lead to presbyopia, light scattering and cataracts, occur simultaneously and continuously, but at different rates. The possible connection between the two processes was clarified by Cook and Koretz, et al. (Invest. Ophthal. Vis. Science (1994)), the entirety of which is specifically incorporated herein by reference to the extent not inconsistent with the disclosures of this patent. Koretz, et al. studied extensively the presence of zones of light scatter. They not only confirmed that older lenses had more light scatter, but also they reported an acceleration in the rate of formation of light-scattering macromolecular complexes starting in the fourth decade of life. Koretz theorized that reduced lens movement due to decreased accommodation reduces the active transport leaving only diffusion and exacerbates the process leading to light scattering.

In order to understand the impact of the methods and systems disclosed herein, it is important to clarify the lens structure with its different segments or shells that form during the ageing process. Thus, as further foundation for this discussion, the anatomical structures of the eye are further shown in FIG. 1, a cross sectional view of the eye. The sclera (31) is the white tissue that surrounds the lens except at the cornea. The cornea (1) is the transparent tissue that comprises the exterior surface of the eye through which light first enters the eye. The iris (2) is a colored, contractible membrane that controls the amount of light entering the eye by changing the size of the circular aperture at its center (the pupil). The ocular or crystalline lens (3), a more detailed picture of which is shown in FIG. 2, is located just posterior to the iris. Generally the ocular lens changes shape through the action of the ciliary muscle (8) to allow for focusing of a visual image. A neural feedback mechanism from the brain allows the ciliary muscle (8), acting through the attachment of the zonules (11), to change the shape of the ocular lens. Generally, sight occurs when light enters the eye through the cornea (1) and pupil, then proceeds past the ocular lens (3) through the vitreous (10) along the visual axis (4), strikes the retina (5) at the back of the eye, forming an image at the macula (6) that is transferred by the optic nerve (7) to the brain. The space between the cornea and the retina is filled with a liquid called the aqueous in the anterior chamber (9) and the vitreous (10), a gel-like, clear substance posterior to the lens.

Generally, the optical characteristics of the eye are determined by the clear tissue and fluids between the cornea (1) and the retina (5). The cornea (1) is a stiff, transparent tissue with a stable curvature confining and protecting the eye contents. The cornea (1) has passive optical characteristics compared with the crystalline lens (3) where the flexible optics actively change refractive error. This is the only structure in the eye that contributes to a change in focusing. In a posterior direction into the eye, there is the fluid called the aqueous (9), then the crystalline lens (3) and the vitreous (10). The fluids of the eye, the aqueous and the vitreous have very little impact upon refraction because they are so close to the refractive index (i.e., the optical density) of adjacent tissues.

Presbyopia is the loss of focusing that occurs when the crystalline lens loses its flexural characteristics sufficient to require auxiliary focusing—i.e., reading glasses or bifocals. Generally, people begin to lose flexibility in their crystalline lenses in their 40s and by age 50 the lens has negligible flexure. There is regularity about presbyopia development that is innate and varies little with disease except in diabetes where presbyopia can come several years earlier. Virtually all humans eventually lose all lens movement except for the outermost areas of the tissue.

The flexure of the lens (3) is illustrated by the accommodative changes that are present in lenses of different ages. For example, it has been shown that flexure can vary as much as about 12-16 diopters, allowing for about a 6-8 cm focus in a 5-year-old to about 50 centimeters or less for a 50-year-old lens. The ciliary muscle (8) stretches while the lens distends for observing distance, and then relaxes returning the focus at near and the lens returns to its actual shape. In an older lens there is little or no distension of the lens, although researchers have shown the ciliary muscle persists in movement even in older, immovable lenses.

There is an anatomical pattern of the development of the crystalline lens (3) that is a characteristic of age. The decline in accommodation, measured by diopters of accommodation, as well as concomitant clarity changes (e.g., zones of discontinuity or increased light scatter), have a high correlation to age. The net result of these irreversible changes continues unless, as this application proposes, there is a change in the transport of ions/fluids to that area. Such changes in clarity are the age-related changes from light scatter which theoretically might result in a cataract when opacification is too great to continue with useful vision. Cataracts, especially in populations under 70-years-old, are more likely from other types caused by systemic disease or other localized mechanisms.

The physiological explanation of light scatter development is that active oxygen is always present and travels from the aqueous and the vitreous into the lens and through the crystalline fibers. This active oxygen causes covalent chemical bonding between the surfaces of the lens fibers, unless specific antioxidants are present to counter the attachments. Once formed, these attachments not only produce sites of light scatter, but reduce the movement between individual fibers. As noted previously, the most common bonds are referred to as disulfide or covalent chemical bonding, which form at a relatively low energy level of chemical bonding. This reduction in movement and bonding produces cascading modification of localized tissue, including compaction and reduction in ionic/fluid transport.

In the ophthalmic literature going back to the early 1900's a paradoxical observation was observed in incidences where foreign bodies such as iron, glass or copper wires enter the eye and sometimes embed in the lens. In most occurrences, the lens becomes cataractous. However, as early as the 1900's, there were reports of embedded objects without cataract development. Some years later, it was shown that these objects did not cause massive infections or inflammations, or affect other ocular tissues, when they were sufficiently small to allow the lens capsule to reseal itself. The significance of this observation was that a foreign body could remain for periods of generally up to 40 years without developing inflammation or a localized or complete cataract. Imbedded foreign bodies demonstrate the inert properties of a crystalline lens without a significant reaction to the outside penetration.

SUMMARY

Because of these and other problems in the art, described herein, among other things, are systems and methods of laser treatment of the intact crystalline lens to increase ionic transport of antioxidants in specific areas where flexural changes and transparency reduction come from lens aging. Microchannels created in patterns and grids placed strategically in the inner lens carry antioxidants from the source—the anterior and the epithelium—into areas scarce or void of transport mechanisms (and thus scarce of antioxidants). A variety of patterns are utilized to facilitate ions traveling along new pathways to produce what is referred to as an "antioxidant lens sink." Transport of antioxidants and its impact upon active oxygen results in lens tissue modifications leading to less light scatter and the rate of development also slows the cascading changes. If this can impact upon the number of free oxygen molecules in the lens, described in the vitrectomy discussion below, then the concentration of oxygen within the aqueous or vitreous may also be affected, reducing oxygen partial pressures near other ocular structures. It is suggested that oxygen partial pressures within the angles (Siegfried 2010) near the trabecular meshwork is associated with individuals with age-related or diseased induced glaucoma. Also disclosed herein is an intraocular implant adding an antioxidant storage capacity which mollifies the oxidative changes of other tissues after cataract surgery.

There is described herein, among other things, a method for improving ionic flow in the crystalline lens of an intact mammalian eye, the method comprising: providing a laser apparatus, the apparatus being capable of acting on the crystalline lens of a mammalian eye; forming a microchannel in said mammalian eye by: maximizing the return of flexure by laser means through channels which synergize ionic flow through the channels; utilizing said laser apparatus to generate a pulse within said mammalian eye, said pulse separating adjacent cellular structures in said mammalian eye; repeating said utilizing a plurality of times to generate a series of pulses, said series of pulses forming a microchannel; forming a microchannel pattern in said mammalian eye by: repeating said forming of a microchannel to form a plurality of said microchannels; and providing a source of ions to said microchannel pattern.

In an embodiment of the method, said series of pulses comprises pulses applied next to each other such that one pulse overlaps with the next and said microchannel is a continuous pathway. In an alternative embodiment, said series of pulses comprises pulses applied next to each other such that one pulse does not overlap with the next and said microchannel is semi-solid.

In an embodiment of the method, said microchannel pattern is a grid pattern with microchannels interconnecting with each other.

In an embodiment of the method, said microchannel pattern is outside the visual axis of the mammalian eye.

In an embodiment of the method, said microchannel pattern has more microchannels traveling along an anterior-posterior direction in the mammalian eye, than from side to side in the mammalian eye.

In an embodiment of the method, at least one microchannel extends into at least one of the adult, juvenile, infantile, or embryonic nucleus.

In an embodiment of the method, at least one microchannel includes an appendage of pulse clusters.

There is also described herein a method for improving fluid flow in the crystalline lens of an intact mammalian eye, the method comprising: providing a laser apparatus, the apparatus being capable of acting on the crystalline lens of a mammalian eye; forming a microchannel in said mammalian eye by: utilizing said laser apparatus to generate a pulse within said mammalian eye, said pulse separating adjacent cellular structures in said mammalian eye; repeating said utilizing a plurality of times to generate a series of pulses, said series of pulses forming a microchannel; forming a microchannel pattern in said mammalian eye by: repeating said forming of a microchannel to form a plurality of said microchannels; and providing a source of fluid to said microchannel pattern.

DESCRIPTION OF THE PREFERRED EMBODIMENTS

Figure 1:
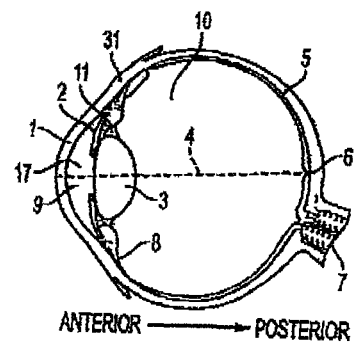
FIG. 1 provides a prior art image of a regular eye.
Figure 2:
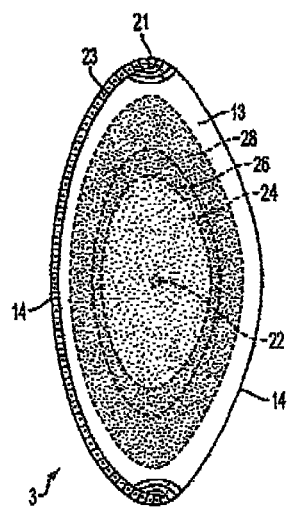
FIG. 2 provides a prior art image of a lens of an eye.
Figure 3:
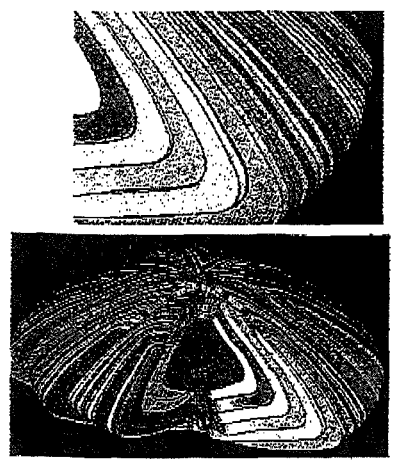
FIG. 3 provides a prior art lens shell drawing.

This disclosure is intended to teach by way of example and not by way of limitation. In the systems and methods disclosed herein, a laser is used to modify the lens tissue that focuses into the crystalline lens of an intact eye. Specifically, lasers (or a similar source of electromagnetic energy known to those of ordinary skill in the art) are utilized to construct microchannel networks to reestablish ionic/fluid transport for stopping or preventing presbyopia progression in some populations (e.g., in 20 or 30 year old eyes) and extending the length of effectiveness of presbyopic lenticular refractive surgery such as that described in U.S. Pat. No. 7,655,002, the entire disclosure of which is incorporated herein by reference to the extent not inconsistent with the disclosures of this patent. Further, extending transport to other lens areas generally has the ability to reestablish the lens as an antioxidant sink for the prevention of cataracts and other ocular diseases associated with the prevalence of active oxygen such as age-related glaucoma and macular degeneration. Finally, an intraocular lens implant is disclosed for use after cataract surgery that also functions as an antioxidant sink, using a regenerating antioxidant stored in the lens periphery to prevent certain ocular diseases.

One important biochemical basis for maintaining crystalline lens clarity is an antioxidative system called glutathione (GSH) redox cycle. GSH is produced by the lens from glucose and is formed from three amino acids: glycine, cysteine, and glutamic acid, which are synthesized in the lens epithelium. Throughout life, the lens is exposed to active oxygen. For example, energy from ambient UV light further enhances oxidative reactions to the fibers including disulfide bonding, especially in the deeper and older lens tissue layers. The GSH redox cycle is very rapid and effective in producing glutathione reductase that combines with the oxygen ions in a catabolic process otherwise eliminating an oxygen molecule which would produce an intracellular connection and light scatter site between two fibers. The GSH is eventually regenerated to its reductase state and is transported throughout the lens in individuals up to 30-years-of-age.

In general, there is some doubt how certain ions, such as GSH, are transported through the lens and whether they move as ions between intracellular spaces or in a fluid media. Fibers are prolific with gap junctions through which transport occurs between fibers. However, it is still uncertain whether with its low water content there may be fluid flow through less tight junctures such as the sutures.

As noted previously, oxygen forms covalent bonding which, over time, alters movement and light scatter. Physical changes occur as the fibers attach, coalesce, and compact in deeper and older tissues. Sweeney and Truscott (Exp. Eye Res. 1998 November) and Truscott (Opth. Res. 2000 September-October) hypothesize that a barrier develops around age 30 at a relatively shallow depth, keeping the GSH from moving into the inner layers. This causes a further cascading reduction of lens hardening starting first in the deeper and older fiber layers.

The principle of ionic/fluid transport can be simply visualized by a wet sponge suspended in a container of water. Liquid flow into the sponge is enhanced by an external force squeezing or stretching the lens. The alternative of no external force or change to the lens leaves only osmosis to pass water molecules, which yields negligible exchange since transfer in osmosis is a function of kinetic energy of the molecules. In the younger eye, the crystalline lens is flexible by the external forces of the ciliary muscle, and to a lesser extent by an elastic lens capsule which facilitates transfer of the force to the entire lens. The movable lens is analogous to the sponge with enhanced fluid transfer by external forces. In the eye, the fully presbyopic lens is immovable without any effective external forces. This coincides with the sponge without external forces and allows only osmosis. The crystalline lens is not as isotropic as the sponge, and researchers and surgeons have to be familiar with lens anatomy of different ages. Some of this necessarily requires new research. The lens is a complex tissue with the older tissues generally harder and with less likelihood of allowing fluid or ionic flow than the younger tissues.

Figure 4:
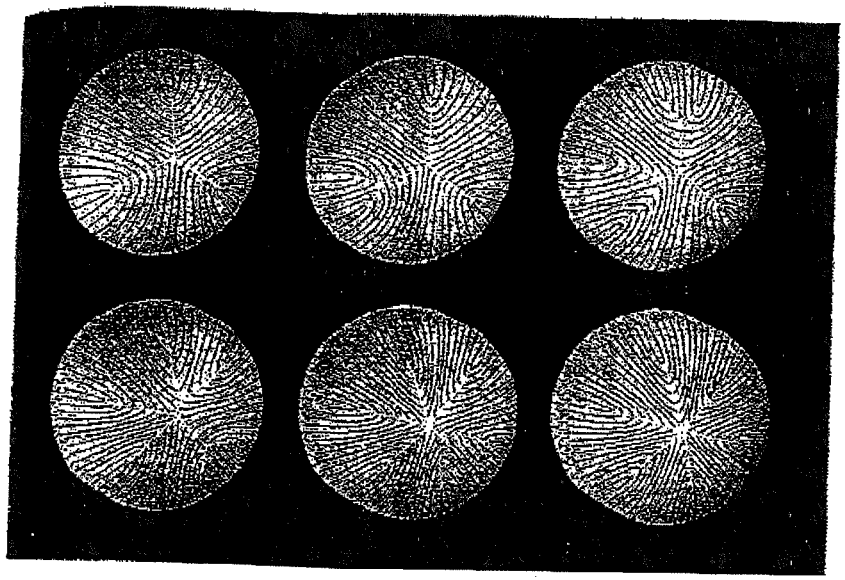
FIG. 4 provides a prior art lens suture drawing.
Figure 5:
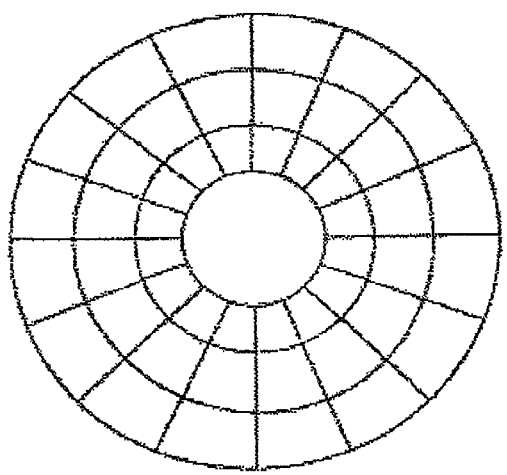
FIG. 5 provides images of a concentric pattern of microchannels with central sparing.
Figure 6:
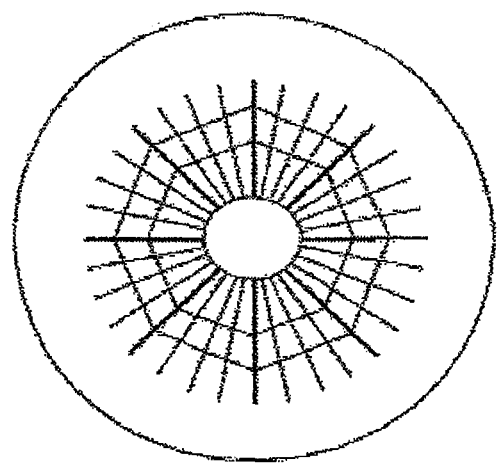
FIG. 6 provides images of sutural & radial pattern of microchannels with central sparing.
Figure 7:
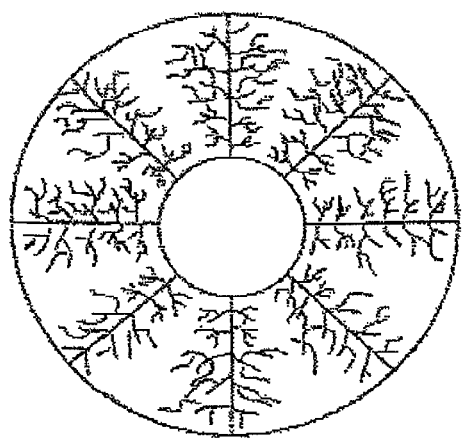
FIG. 7 provides images of concentric pattern of microchannels with central sparing, limb-like structures, and pods.
Figure 8:
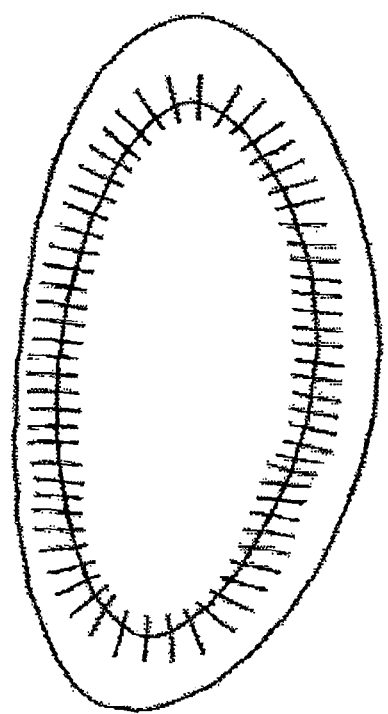
FIG. 8 provides images of microchannel passages through the Truscott Barrier.
Figure 9:
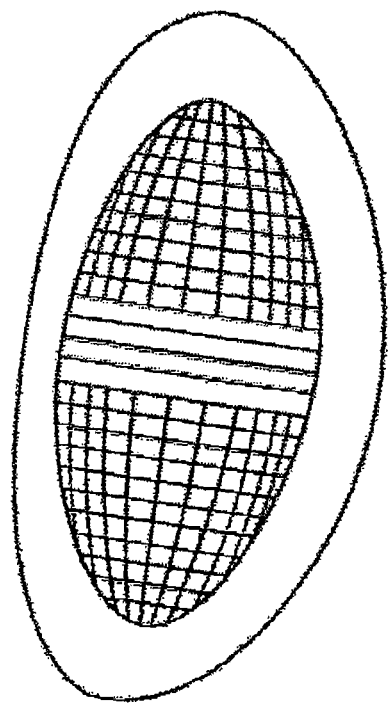
FIG. 9 provides a side view of a grid-like pattern of microchannels.
Figure 10:
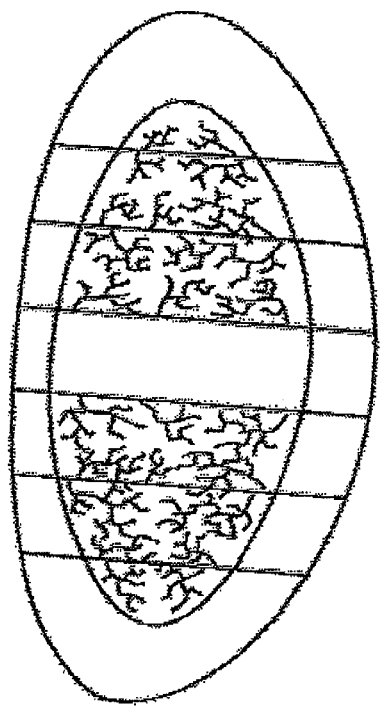
FIG. 10 provides a side view of microchannels with limb-like structures and pods.
Figures 11, 11A:
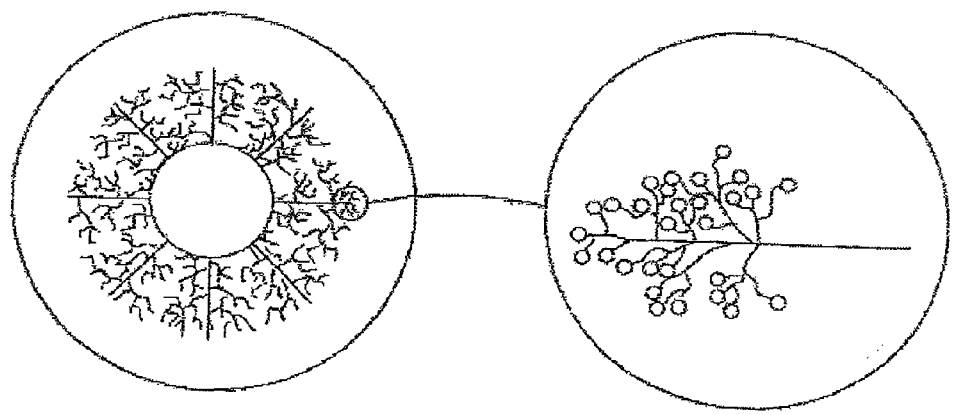
FIG. 11 provides a front view of the sutural pattern of FIG. 10 with limb-like structures, pods, and central sparing.
FIG. 11A provides a detail area of FIG. 11 showing an embodiment of grape pods.

As further foundation for the disclosure discussed herein and as will be understood by those of ordinary skill in the art, it is noted that throughout life of the lens, crystalline fibers generally form at the lens equator from a layer of germinal epithelium (21), and move anteriorly and posteriorly with a regularity that is generally determined by previous fibers. These crystalline fibers generally end with the fibers from opposite directions on the equator forming the sutures, as demonstrated in FIG. 4. The lens has a different biconvex shape at various ages as a result of discernible difference in fibril shapes with different numbers of sutures. They roughly are illustrated by the "Y" describing the 3 arms to a 15 suture star pattern seen in some older adults over the age of 50.

Fibers laid down in childhood generally grow at a more rapid pace with each contributing to an enlarging lens compared with what happens during later life. The relative hardness in various areas of the young and the old lens change. Whereas in the younger lens the outer part of the lens (the cortex) is harder, the cortex of the old lens is softer than the various nuclei and the crossover point where they are both equal is about age 30. The result is that throughout life the hardness, and therefore the elasticity and flexibility, of the shells is changing at different levels. The significance of this includes another change called compaction in the deeper fibers with older lenses that reduce thickness changes at the same time as more fibers are added to the outer surface. One lens modification factor incorporating the differences in the hardness between corresponding points of nuclei of different human lenses of various ages is that the shell-like structure of the crystalline lens, combined with the different compaction and rigidity of different areas, make certain areas more beneficial to modification.

While the utilization of electromagnetic energy to make physical and biochemical alterations to the eye to decrease the hardening and increase the flexibility of the eye are known, these systems and processes are not known to have an effect on the transportation of antioxidants, such as GSH, throughout the lens structure, a process which decreases with age as detailed above. Accordingly, there is a need in the art for methods of modifying or altering the eye structure to maintain a consistent (or, at least a minimally required flow) of antioxidants (predominantly GSH) throughout the lens structure as the eye ages.

In the current disclosure, different patterns and strategies are used that have little or no contribution to flexural or shape changes, but rather impact the durability of the surgery and enhance mechanisms to reduce the development of cataracts or other associated eye diseases. As noted previously, cataract retardation is a reduction in the development of light scatter, the precursor to cataracts. Stated differently, a purpose of the systems and methods disclosed herein is to form new pathways, grids, and channels into the deeper and older lens tissues to reduce further oxidative and light scatter changes common to certain locations because of the non-penetration of glutathione.

The modifications of the systems and methods disclosed herein involve using various algorithms and shapes that improve flexure or shape or volume, but the major modifications described herein are predominantly those that directly cause and improve ionic or fluid transport within the internal lens. Transport properties are modified mainly with channels that travel to areas where further transport occurs through cell junctions, fibrous cytoplasm, and between the interstices of the fiber.

The microchannels described herein (which are generally created by the use of laser apparatus or another form of electromagnetic energy known to those of ordinary skill in the art) are channels specifically for increasing ionic flow that comprise of one or more separate pulses, or microspheres, and are joined and traverse in a predetermined direction. Depending upon whether the ultimate ionic transport is in a liquid medium or a semi-solid medium or space, the microchannel may be empty such as in a row of joined pulses, or it might be a line of separate pulses where a lesser density in the particular shell is sufficient to improve ionic flow, or it might be a pattern of partially separated pulses that facilitate through an active surface the movement of ions. Thus, in general, the microchannels discussed herein can be thought of as open channels that enable the flow of liquid. Alternatively, they can be thought of as a sieve-like, three-dimensional structure that favors the travel without fluid of the GSH along an active channel surface.

As noted previously, it is hypothesized that the shell-like structure of the crystalline lens, combined with the different compaction and rigidity of different areas, make certain areas more beneficial to modification and microchannel formation. The modifications described herein are predominantly those that directly cause and improve ionic transport within the internal lens. Transport properties are modified mainly with channels that travel to areas where further transport occurs through cell junctions, fibrous cytoplasm, and between the interstices of the fibers.

As covered in the Background, with the advance of age, the changes to and hardening of the lens accelerates. The microchannel networks contemplated and discussed herein, among other things, increase the transport of GSH, which counteracts the oxidative changes allowing the flexural condition to be maintained. By placing a network of channels and locations which otherwise remain open, the goal of the changes is to maintain antioxidant transport in tissues that otherwise contribute to a cascading reduction of movement and inversely an increase in light scatter. By preparing a network of channels, grids, and end paths which increase or at least maintain antioxidant flow in the eye structure, the systems and methods disclosed herein, if performed in a younger eye, could stave off presbyopia development by 10 or 15 years into the mid-fifties.

Accordingly, in one embodiment disclosed herein, microchannel formation will be performed as a concomitant procedure to other electromagnetic-based ocular surgical procedures an individual might receive in his/her 20s or 30s. For example, individuals in their 20s and 30s can have lenticular refractive surgery, such as that disclosed in U.S. Pat. No. 7,655,002, to correct common refractive errors such as myopia and hyperopia. Notably, in the current state of the art, these procedures are utilized to address refractive errors in the lens, not to prevent presbyopic changes that manifest 10-20 years later. In one embodiment of the systems and methods described herein, it is contemplated that those individuals having surgery for other refractive errors such as myopia or hyperopia have a concomitant procedure which creates microchannels for ionic fluid transport and bypassing the natural barriers, for example of the Truscott barrier described below, that are common to that age category. The introduction of the microchannel networks described herein into an individual at a younger stage of eye-age are expected to result in a maintenance of ionic transport to eye tissues and slow up the changes which produce a specific decline in accommodation at succeeding ages. The net result is that instead of a person developing presbyopia around 45, the modification holds off the development until age 55 or later, thus extending the period before presbyopia. Furthermore, it is hypothesized that the inert characteristics of lens fibers would make the formed channels unlikely to change over extended periods of time, much like foreign bodies that embed in lenses.

Thus, it is hypothesized that the surgical formation of the microchannel ionic fluid pathways disclosed herein in an individual in his/her 20s or 30s could produce presbyopia retardation. At this age, a person would want a correction of his/her myopia or hyperopia such that a key difference between corneal refractive surgery or LASIK would be the future extension of life without presbyopia for some period of time. For lenticular refractive surgery in comparison, the ability to correct presbyopia provides an additional feature without parallel in corneal refractive surgery. Notably, the surgical formation of the microchannel ionic fluid pathways in these populations is carried out by a different mechanism than for accommodative restoration or flexural improvement. The presence of a better ionic/fluid transport system in certain sites keeps the flexure longer and the increasing flexure adds to the efficacy of the ionic flow changes.

Alternatively, the surgical formation of the mirochannel ionic fluid pathways disclosed herein is performed later when the patient is presbyopic. At this time, presbyopia correction includes accommodative restoration, and the additional strategy for the transport changes is to reduce age related changes that might be predicted after surgery. Thus, the systems and methods for microchannel formation disclosed herein, in certain embodiments, will have a different role when used in individuals between the ages of 45-50+ because certain patterns are used to stave off further hardening of tissues that would otherwise continue. For example, the systems and methods disclosed herein can be utilized to establish a better antioxidant sink. These modifications include microchannels, but are not be necessarily limited to them, and will include networks and end channels appropriate to the patient age and specific lens physical condition.

In sum, described herein are systems and methods for lens modification which can be classified into 4 groups.
- Laser-Assisted Cataract Surgery: In the lens for cataract fragmentation, anterior capsulotomy, capsulorhexis and posterior capsulotomy.
- Lenticular Refractive Surgery: For the purpose of modifying lens for correction of presbyopia (accommodative restoration), myopia, hyperopia, astigmatism, and other ametropias.
- Ocular Disease Prevention: Cataract retardation, and cataract, glaucoma, vitrectomy, and macular degeneration prevention.
- Presbyopia Prevention and Extension: Modify the crystalline lens through internal channels and networks, grape pods, such that the crystalline lens retains its flexural characteristics by a superior form of ionic/or fluid flow.

Thus, disclosed herein, among other things, are methods to treat the crystalline lens in individuals and create a sink or reservoir for antioxidant storage and for the reduction of free oxygen radicals. A purpose is to reduce the concentration of oxygen ions in the lens and also the concentration of radicals in the aqueous and vitreous, leading to retarding cataract development and preventing other eye disease such as aged-related glaucoma and macular degeneration. The systems and methods disclosed herein define transport methods, sometimes enhanced by flexural changes, that protect and extend the accommodative and refractive treatment by years beyond what might be expected without transport methods. The methods capitalize on the potential of the movable lens to produce more effective transport of ions, and especially glutathione reductase (GSH) against oxygen molecules, that are from within and outside the lens.

Since GSH is concentrated in the epithelium, as discussed above, a strategy of the system and methods disclosed herein is to enhance the transport of the GSH ions into deeper layers where they are needed to counteract the oxygen presence. The microchannels may well travel to multiple shells and areas and also serve wide areas. Microchannels may also parallel sites such as the sutures where the movement of ions is enhanced just as concentrating on the epithelial area because of representing the best source of transfer in a particular series of shells. They may be essentially multi-concentric, or multiple shells conforming well to the lenticular shape below it.

In one contemplated embodiment, depending upon the flow of ions either in a liquid or dry medium, a grid-like pattern of microchannels is utilized to increase coverage and maintain redundant coverage in similar areas. An embodiment of a grid-like pattern of microchannels is provided in FIG. 9. Further, in another embodiment, where it is necessary to achieve a dense coverage in a particular area or an end pattern, it is possible to produce a grape-like configuration with or without an actual protuberance like a grape ("grape pods") at the extremities that exposes a larger area to a spherical opening. As will be understood by those skilled in the art, this might be done at the sutures where many sutures are positioned next to each other. It is also possible to use cleavage to open pathways perhaps nearby sutures where adjoining ends of contiguous fibers are then loosened. Lastly, density changes occur through applying an even but detached pattern of pulses, extending through the Truscott ring. Different contemplated embodiments which depict multiple different microchannel orientations are depicted in FIGS. 5-11.

Generally, all of the passages of the microchannels disclosed herein spare the central area of the lens to protect the optical center that otherwise effects the pathways of light. It is also possible to place microchannels strategically so as not to interfere, for example by having microchannels nearly parallel the optical axis of the lens and a two-dimensional pattern facing the oncoming light.

Based, in part, upon the forgoing, this disclosure includes the following four components that are further described in later paragraphs. They comprise, among other things, embodiments and components of the present invention:
1. The crystalline lens as a reservoir and sink for antioxidants and for prevention of ocular diseases;
2. Prevention of presbyopia by ionic/fluid transport in an adult eye of approximately 20-30 years of age;
3. Lengthening the accommodative restoration effects among patients treated for lenticular refractive surgery;
4. An intraocular lens with stored antioxidants which produces an artificial antioxidant sink or reservoir to absorb and reduce free oxygen radicals.

The Crystalline Lens as a Reservoir & Sink for Antioxidants and for Prevention of Ocular Diseases In an embodiment described herein, the disclosure identifies the lens as an antioxidant sink or reservoir which is far more efficient with the return of flexure and removing barriers through creating pathways. Generally, the surgical treatment of the lens increases the surface area to expose the antioxidant to oxygen ions, which deplete the oxygen ions within the lens, but ions flow readily from the fluids (the aqueous and vitreous) and this reestablishes an antioxidant sink much like the youthful lens. Further, this may influence the partial oxygen concentrations elsewhere in the eye. The partial oxygen levels in the angle adjacent to the trabecular meshwork within are likely to be lowered. Siegfried (2010) has noted that the partial oxygen levels vary markedly depending upon race in older patients known to have a greater incident of glaucoma, and among patients with particular surgeries such as vitrectomy (discussed below), aphakia and glaucoma.

In an embodiment described herein, this disclosure also proposes that the flexible lens is a sink or reservoir capable of neutralizing the active oxygen present throughout the eye that may lead to macular degeneration. Further, the flexible lens, in combination with the active vitreous antioxidant sink described below neutralizes active oxygen at the macula (6).

By aging without the recommended treatment, the 45-50 year old lens loses its ability to move because of years of cascading changes in increasing hardness and decreasing ionic permeability. The physiological basis is the glutathione redox cycle—where glutathione reductase (GSH) is first produced anteriorly in the epithelium. GSH reductase travels to the deeper tissues, reacting with oxygen ions and producing glutathione perioxidase. This eliminates the alternative oxidative modifications on the crystalline surfaces that are largely intrafibril disulfide bonding. Glutathione perioxidase then returns to the epithelium layers and, after conversion to reductase, recycles to the deeper layers. Age reduces the transport. It is likely that, at older ages, creating a demand for GSH by the laser lens modification will increase the production of GSH. Sweeney and Truscott (1998) notes that there is a barrier that forms as early as age 30 in significant number of tissues. The active oxygen molecules are not constrained from being transported into the deeper tissues so much as the GSH. The active oxygen in the deeper tissues remains creating the disulfide bonding largely from the energy provided by ambient UV light.

Figure 12:
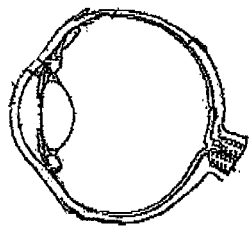
FIG. 12 provides sectional views of various different types of eyes.
Figure 12:
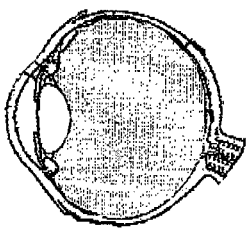
Figure 12:
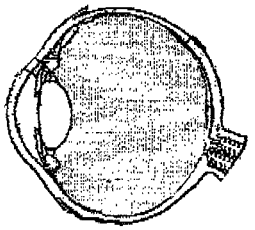
Figure 12:
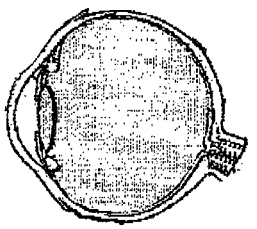

In later paragraphs, the significance of antioxidant sinks in the eye is discussed in detail. In general, four different conditions can be demonstrated by three different parameters: (1) individual age groups—presbyopia (>Age 50) or non-presbyopia (<Age 40); (2) an effective or non-effective sink in either the lens or vitreous; and (3) presence or absence of a lens or intraocular lens or vitreous acting as a barrier. In FIG. 12, as will be understood by those of ordinary skill in the art, Eye A demonstrates a normal eye of a non-presbyopia where the lens has significant glutathione transport as well and the vitreous has antioxidant transport. Eye B demonstrates a vitrectomy in a presbyopic eye, leaving only the lens which itself is an obstacle, and no vitreous. Cataracts are likely to occur within a year. Eye C is a non-presbyopic or young (<40 years) eye with a vitrectomy removing the vitreous sink. The major difference between Eye C and Eye D is the flexural characteristics of the lenses. Thus, a cataract will develop slowly or not at all depending upon the patient and, therefore, the associated lens movement. In Eye D, the lens has been removed and replaced with a regular intraocular implant and the vitreous has also been removed. Siegfried showed by comparing groups of surgically treated patients that at the angle there are statistically greater oxygen partial pressures in comparing Eye D with Eye B, and Eye D and Eye A. In Eye B, without a vitreous sink and with a non-functional sink with the lens, a cataract develops within a year because nothing stops the buildup of the oxygen traveling through the fluid.

The vitreous of the eye is adjacent and posterior to the lens, and acts as a sink containing a continual supply of the antioxidant ascorbic acid (Vitamin C). Ascorbic acid is replenished from the aqueous (Bai 2010), and comes from outside the body. When the vitreous is removed in vitreal retinal surgery, fluid refills the cavity and the oxygen molecules coming from retinal vessels travel more freely through a liquid medium. Increased partial oxygen pressure in other parts of the eye occurs in patients over 50, and the inevitable development of a cataract also happens within two years of surgery.

Holekamp (Melberg) and Thomas' earlier research with vitrectomy in 1995 demonstrated a paradox where the mechanism or cause was not explained at the time. They concluded that vitrectomies among non-presbyopes (i.e., less than age 40) were less likely to develop cataracts in the short term, compared to the presbyopia group. In infants with vitrectomies Maguire (1992) and Moshfeghi (2004) showed that infants rarely produce a cataract within five years of surgery.

The major difference between these populations is the flexure of the lens which is present until the mid-40s. The movable crystalline lens has mechanical forces transferred through the fibers, which contribute to ionic/fluid transfer either through fluid flow or cellular transfer. An analogy is the previously discussed sponge which absorbs fluids fast if the sponge is being squeezed and released rather than an immovable sponge.

Further, after vitrectomy substantially higher ionic concentrations travel through the eye and the removal of the gel-like posterior contents eliminated the shield for oxygen molecules from the retinal vessels (3) in the posterior eye. When Beebe and colleagues looked at mechanisms, they hypothesized that the barrier to oxygen transport through the vitreous was the stored ascorbic acid and the gelatinous nature, which reduced active oxygen flowing through the anterior of the lens.

If the crystalline lens has its movement characteristics restored with increasing ionic flow through channels, then the active oxygen is more likely to receive glutathione, and produce a net reduction in oxygen concentrations. Such diseases as cataracts in vitrectomies and glaucoma have been shown to be partly a result of the effects of oxidative modifications to local tissues, such as in the lens fibers in cataracts, and in the trabecular meshwork of the angle in glaucoma.

A further observation is that from clinical studies it is known that African-Americans have a greater incidence of glaucoma than Caucasians when ages are matched. Siegfried, et al. (2010) noted that partial oxygen pressures were higher among African-Americans with glaucoma, compared with other African-Americans without glaucoma. Both groups had higher partial oxygen pressures in the angle than Caucasians. Active oxygen concentrations appear to be explained by a physiological difference of the trabecular meshwork, known also to be age related and race related. The meshwork thickens and become sclerotic with age, and had been previously observed, creating an aqueous obstruction out of the globe leading to increased intraocular pressure.

Whereas vitrectomy is an excellent medical model for demonstrating cataract development, and the effects of increased antioxidants in the eye, cataracts secondary to vitrectomy should be preventable. In the presbyopia, returning flexure and fluid flow within the crystalline lens could restore one sink to act against internal oxidative buildup.

Prevention of Presbyopia by Ionic/Fluid Transport in an Adult Eye of Approximately 20-30 Years of Age.

The intent of lenticular surgery previously known in the art was to modify the crystalline lens of the eye for the primary purpose of reestablishing the flexural characteristics of the lens and to change its shape to correct different forms of ametropia (i.e., myopia, hyperopia, and astigmatism). Until then, there was no possibility of retaining or changing lens movement of surgery but a continuation of the changes which account for 100% loss by the age of 50. The methods described herein are not to modify the tissues for flexural or shape purposes. Rather, they are intended to establish microchannels and interlocking networks that, when done on younger tissues, reduce the "hardening" mechanisms in specific lens areas. These modifications are designed to produce changes in areas of the lens that are most susceptible. For example, outer shells formed within the past three to eight years are more amenable to change than areas in the internal depths where compaction and other processes result in an immutable tissue. Another example is the younger lens where the nuclei are likely to be more flexible and changeable than the 50 or 60-year-old lens. The 30 or 40-year-old is likely to be having surgery for the immediate gratification of correcting refractive error, but the possibility of having a surgical procedure that reduces presbyopic changes years later may be a competitive feature of lenticular refractive surgery. Corneal refractive surgery, in comparison, will not return natural accommodation. After the surgical plan for lenticular refractive surgery is determined considering the changes needed for a specific amount of hyperopia or myopia, as well as reestablishing presbyopia, certain changes using algorithms build an ionic/fluid flow that extends the effects of shape and flexure change. Whereas a younger person, for example, a 20 or 30-year-old, is likely to have sufficient accommodation not to require accommodative restoration, the changes made during surgery have the potential of keeping presbyopia from settling in at the same ages this would happen otherwise. For example, virtually all have presbyopia inevitably starting in the mid-40s but this type of surgery when done 10 or 20 years earlier, averts the physiological certainty of presbyopia, readers, and bifocals in the middle 40s.

With this in mind, transport is defined within this disclosure to be movement of ions in a liquid, molecular, or spatial network that either exists normally or is restored by the placement of microchannels, networks, or end patterns that specifically carry antioxidants in greater abundance than would otherwise occur. It is contemplated that the diameter of the pulse, or the energy levels may need to be varied in order to optimize the transport of ions.

Lengthening the Accommodative Restoration Effects Among Pre-Presbyopes and Previously Described Lenticular Refractive Surgery.

Previously disclosed in the art are methods and treatments by which crystalline lens flexure is reversed or improved. However, after the known prior art treatments to improve or reverse flexure, currently flexure is still expected to decline just like before surgery. This is because while the treatments previously known in the art correct flexure issues, they do not make the physical lens changes which causes accommodation to decline. This application now discloses different methods to produce a longer lasting effect for the treatment by improving lens ionic/fluid flow.

When accommodative restoration occurs, the surgery restores a level of accommodation or focusing for close up work. However, future deterioration still continues after surgery by the same principles that caused change before the surgery. The antioxidant sink methods treat areas that are intended to reduce future changes and presbyopic modifications. Therefore, the surgeon and instrumentation determine the extent that the patient matches his/her age category. Then, based upon the patient age at surgery combined with any departure from the normal, the computer software translates the modifications with microchannels and interlocking networks to the best locations for maximum benefit.

The goals of these changes include preventing presbyopia by ionic/fluid transport, and they depend upon patient age at surgery. They are independent sets of algorithms previously mentioned for flexural change, and are performed in the lens location of older patients where much more tissue is supplied with the proper channels and fluid flow.

An Intraocular Lens with Continual Antioxidants Produces an Artificial Antioxidant Sink or Reservoir to Absorb and Reduce Free Oxygen Radicals.

Also disclosed herein is a new and improved intraocular lens which is a reservoir for antioxidants for the purpose of retarding or preventing eye disease, in addition to its traditional function of refracting the light that focuses at the fovea. The purpose is to develop a sink or reservoir to reduce the quantity of oxygen. Chemical compounds are hereby chosen to establish an oxidation and oxidative-reduction equilibrium that is influenced either by pharmaceuticals ingested or topically administered that rejuvenate the stored antioxidants by energy delivery of a laser or light to reverse the treated antioxidant in the reservoir.

Generally, the traditional intraocular lens consists of about a 6-7 mm optical section having a particular power which, in combination with the eye, corrects for the removal of the original lens. Thus, a replacement lens could be provided with microchannels already present as part of a lens transplant.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

The invention claimed is:

1. A method for improving ionic flow in the crystalline lens of an intact mammalian eye, the method comprising:
   providing a laser apparatus, the apparatus being capable of acting on a crystalline lens of a mammalian eye;
   using said laser apparatus, forming a microchannel in said crystalline lens of said mammalian eye by:
   utilizing said laser apparatus to generate a pulse within said crystalline lens of said mammalian eye, said pulse removing a targeted portion of said mammalian eye; and
   repeating said utilizing a plurality of times to generate a series of pulses, said series of pulses forming a microchannel;
   wherein said microchannel comprises a line of pulses wherein:
   said removed portions are spatially separate; and
   a lesser density in a particular shell of said crystalline lens, through which said microchannel passes, is sufficient to facilitate ionic transport through said microchannel without said removed portions joining to form an open channel that enables a flow of liquid; and
   forming a microchannel pattern in said mammalian eye by:
   repeating said forming of a microchannel to form a plurality of said microchannels; and
   wherein, at least one microchannel has an appended pod formed of clustered pulses extending therefrom.

2. The method of claim 1, wherein said microchannel pattern is a grid pattern having microchannels at least partially separated from each other.

3. The method if claim 1, wherein said microchannel pattern is outside the visual axis of said mammalian eye.

4. The method of claim 1, wherein said microchannel pattern has microchannels at least partially separated from each other.

5. The method of claim 1, wherein at least one microchannel extends into at least one of the adult, juvenile, infantile, or embryonic nucleus.

6. A method for improving ionic flow in the crystalline lens of an intact mammalian eye, the method comprising:
   providing a laser apparatus, the apparatus being capable of acting on a crystalline lens of a mammalian eye;
   using said laser apparatus, forming a microchannel in said crystalline lens of said mammalian eye by:
   utilizing said laser apparatus to generate a pulse within said crystalline lens of said mammalian eye, said pulse removing a targeted portion of said mammalian eye; and
   repeating said utilizing a plurality of times to generate a series of pulses, said series of pulses forming a microchannel;
   wherein said microchannel comprises a line of pulses wherein:
   said removed portions are spatially separate; and
   said removed portions facilitate, through an active surface, the transport of ions through said microchannel without said removed portions joining to form an open channel that enables a flow of liquid; and
   forming a microchannel pattern in said mammalian eye by:
   repeating said forming of a microchannel to form a plurality of said microchannels; and
   wherein, at least one microchannel has an appended pod formed of clustered pulses extending therefrom.

7. The method of claim 6, wherein said microchannel pattern is a grid pattern having microchannels at least partially separated from each other.

8. The method if claim 6, wherein said microchannel pattern is outside the visual axis of said mammalian eye.

9. The method of claim 6, wherein said microchannel pattern has microchannels at least partially separated from each other.

10. The method of claim 6, wherein at least one microchannel extends into at least one of the adult, juvenile, infantile, or embryonic nucleus.

11. The method of claim 1, wherein fluid is not flowing through said microchannel.

12. The method of claim 6, wherein fluid is not flowing through said microchannel.

* * * * *